US005736524A

United States Patent [19]
Content et al.

[11] Patent Number: 5,736,524
[45] Date of Patent: Apr. 7, 1998

[54] POLYNUCLEOTIDE TUBERCULOSIS VACCINE

[75] Inventors: Jean Content, Rhode-Saint-Genese; Kris Huygen, Brussels, both of Belgium; Margaret A. Liu, Rosemont, Pa.; Donna Montgomery; Jeffrey Ulmer, both of Chalfont, Pa.

[73] Assignees: Merck & Co.,. Inc., Rahway, N.J.; N. V. Innogenetics S.A., Ghent, Belgium

[21] Appl. No.: 338,992

[22] Filed: Nov. 14, 1994

[51] Int. Cl.$^6$ .................. A61K 48/00; C07H 21/00; C12N 15/79; C12N 15/63
[52] U.S. Cl. .................. 514/44; 435/6; 435/69.1; 435/172.3; 435/375; 435/320.1; 935/62; 935/56; 935/34; 935/65
[58] Field of Search .................. 435/320.1, 6, 69.1, 435/172.3, 243, 252.1; 514/44; 935/62, 65, 66, 70, 71, 33, 34, 72

[56] References Cited

FOREIGN PATENT DOCUMENTS

| | | |
|---|---|---|
| WO90/11092 | 4/1990 | WIPO. |
| WO91/04272 | 4/1991 | WIPO. |
| WO92/14823 | 3/1992 | WIPO. |
| WO93/19183 | 9/1993 | WIPO. |

OTHER PUBLICATIONS

Gansbacher et al., "Retroviral vector-mediated cytokine gene transfer into tumor cells," Cancer Investigation, vol. 11 (3): 345–354, Mar. 1993.
Bengard Anderson, Mycobacterium tuberculosis proteins, Danish Medical Bulletin, vol. 41, No. 2, pp. 205–215 (1994).
Bloom and Murray, Tuberculosis: Commentary on a Reemergent Killer, Science, vol. 257, pp. 1055–1064 (1992).
Silva and Lowrie, A single mycobacterial protein (hsp 65) expressed by a transgenic antigen-presenting cell vaccinates mice against tuberculosis, Immunology, vol. 82, pp. 244–248 (1994).
Young and Garbe, Lipoprotein antigens of Mycobacterium tuberculosis, Res. Microbiol. vol. 142, pp. 55–65 (1991).
K. Huygen et al., Specific Lymphoproliferation, Gamma Interferon Production, and Serum Immunoglobulin G Directed against a Purified 32 kDa Mycobacterial Protein Antigen (P32) in Patients with Active Tuberculosis, Scand. J. Immunol., vol. 27, pp. 187–194 (1986).
F. M. Collins, The immune response to mycobacterial infection: Development of new vaccines, Veterinary Microbiology, vo. 40, pp. 95–110 (1994).
F. Romain et al., Isolation of a proline-rich mycobacterial protein eliciting delayed-type hypersensitivity reactions only in guinea pigs immunized with living mycobacteria, Proc. Natl. Acad. Sci., vol. 90, pp. 5322–5326 (1993).
Joanne L. Flynn et al., Major histocompatibility complex class I-restricted T cells are required for resistance to Mycobacterium tuberculosis infection, Proc. Natl. Acad. Sci. vol. 89, pp. 12013–12017 (1992).

Peter Andersen, Effective Vaccination of Mice against Mycobacterium tuberculosis infection with a soluble mixture of secreted mycobacterial proteins, Infection and Immunity, vol. 62, No. 6, pp. 2536–2544 (1994).
Pal and Horwitz, Immunization with extracellular proteins of Mycobacterium tuberculosis induces cell-mediated immune responses and substantial protective immunity in a guinea pig model of pulmonary tuberculosis, Infection and Immunity, pp. 4781–4792 (1992).
Joanne L. Flynn et al., An Essential Role for Interferon γ in Resistance to Mycobacterium tuberculosis Infection, J. Exp. Med., vol. 178, pp. 2249–2254 (1993).
Ian M. Orme et al., T Cell Response tooMycobacterium tuberculosis, J. Infect. Diseases, vol. 167, pp. 1481–1497 (1993).
Wiker and Harboe, The Antigen 85 Complex: a Major Secretion Product of Mycobacterium tuberculosis, Microbiological Reviews, pp. 648–661 (1992).
A. Faith et al., Analysis of human T-cell epitopes in the 19,000 MW antigen of Mycobacterium tuberculosis: influence of HLA-DR, Immunology, vol. 74, pp. 1–7, (1991).
Harboe and Wiker, The 38-kDa Protein of Mycobacterium tuberculosis: A Review, The J. of Infect. Dis., vol. 166, pp. 874–884 (1992).
Pascal Launois et al., T-Cell-Epitope of the Major Secreted Mycobacterial antigen Ag85A in Tuberculosis and Leprosy, Infection and Immunity, pp. 3679–3687 (1994).
P. Launois et al., T Cell response to purified filtrate antigen 85 from Mycobacterium bovis Bacilli Calmette-Guerin (BCG) in leprosy patients, Clin. exp. Immunol., vol. 86, pp. 286–290 (1991).
Martin E. Munck et al., The Mycobacterium bovis 32-kilodalton Protein Antigen Induces Human Cytotoxic T-Cell Responses, Infection and Immunity, vol. 62, pp. 726–728 (1994).

(List continued on next page.)

Primary Examiner—Jasemine C. Chambers
Assistant Examiner—Karen M. Hauda
Attorney, Agent, or Firm—Michael D. Yablonsky; Jack L. Tribble

[57] ABSTRACT

Genes encoding Mycobacterium tuberculosis (M.tb) proteins were cloned into eukaryotic expression vectors to express the encoded proteins in mammalian muscle cells in vivo. Animals were immunized by injection of these DNA constructs, termed polynucleotide vaccines or PNV, into their muscles. Immune antisera was produced against M.tb antigens. Specific T-cell responses were detected in spleen cells of vaccinated mice and the profile of cytokine secretion in response to antigen 85 was indicative of a $T_h1$ type of helper T-cell response (i.e., high IL-2 and IFN-γ). Protective efficacy of an M.tb DNA vaccine was demonstrated in mice after challenge with M. bovis BCG, as measured by a reduction in mycobacterial multiplication in the spleens and lungs of M.tb DNA-vaccinated mice compared to control DNA-vaccinated mice or primary infection in naive mice.

17 Claims, 15 Drawing Sheets

OTHER PUBLICATIONS

Kris Huygen et al., Spleen Cell Cytokine Secretion in *Mycobacterium bovis* BCG–Infected Mice, Infection and Immunity, vol. 60, No. 7, (1992).

Jean Content et al., The Genes coding for the Antigen 85 Complexes of *Mycobacterium tuberculosis* and *Mycobacterium bovis* BCG are members of a Gene Family . . . , Infection and Immunity, vol. 59, No. 9, pp. 3205–3212 (1991).

Martine Borremans et al., Cloning, Sequence Determination, adn Expression of a 32–Kilodalton–Protein Gene of *Mycobacterium tuberculosis*, Infection and Immunity, vol. 57, No. 10, pp. 3123–3130 (1989).

S. E. Parker et al. Intramuscular Vaccination of Plasmid DNA Containing Viral Antigens Provides Protection Against A Lethal Viral Challenge, Modern Approaches to New Vaccines, 16, p. 47 (1992).

G. H. Rhodes et al., A Novel Method of Inducing Cellular and Humoral Immunity to HIV GP120 Protein by DNA Injection, Modern Approaches to New Vaccines, p. 91 (1992).

G. H. Rhodes et al., Injection of Expression Vectors Containing Antigen Genes Induce Cellular and Humoral Immunity to the Antigen, Modern Approaches to New Vaccines, p. 51 (1992).

Wolff and Lederberg, An Early History of Gene Transfer and Therapy, Human Gene Therapy, vol. 5: pp. 469–480 (1994).

N. Zhu et al., Systemic Gene Expression After Intravenous DNA Delivery into Adult Mice, Science, vol. 261, pp. 209–211 (1993).

J. A. Wolff et al., Long–term Persistence of Plasmid DNA and Foreign Gene Expression in Mouse Muscle, Human Molecular Genetics, vol. 1, No. 6, pp. 363–369 (1992).

J. Cohen, Naked DNA Points way to Vaccines, Science, vol. 259, pp. 1691–1692 (1993).

S. Jiao et al., Direct Gene Transfer into Nonhuman Primate Myofibers In Vivo, Human Gene Therapy, vol. 3, pp. 21–33 (1992).

H. Lin, et al., Expression of Recombinant Genes in Myocardium In Vivo After Direct Injection of DNA, Brief Rapid Communication, vol. 82, No. 6, pp. 2217–2221 (1990).

E. Hansen et al., Strong Expression of Foreign Genes Following Direct Injection into Fish Muscle, FEBS 10177, vol. 290, No. 1.2, pp. 73–76 (1991).

H.L. Robinson, Use of Direct DNA Inoculations to Elicit Protective Immune Repsonses, Modern Approaches to New Vaccines, p. 92, (1992).

Benvenisty and Reshef, Direct Introduction of Genes into rats and expression of the genes, Proc. Natl. Acad. Sci., vol. 83, pp. 9551–9555 (1986).

J. A. Wolff et al., Direct Gene Transfer into Mouse Muscle in Vivo, Science, vol.247, pp. 1465–1468 (1990).

D. Tang et al., Genetic Immunization is a simple method for eliciting an immune response, Nature, vol. 356, pp. 152–154 (1992).

T. Dubensky, Direct Transfection of Viral and plasmid DNA into the liver or spleen of mice. Proc. Natl. Acad. Sci. vol. 81, pp. 7529–7233 (1984).

J. B. Ulmer et al., Heterologous Protection Against Influenza by Injection of DNA Encoding a Viral Protein, Science, vol. 259, pp. 1745–1749 (1993).

D. L. Montgomery et al., Heterolous and Homologous Protection Against Influenza A by DNA Vaccination: Optimization of DNA Vectors, DNA and Cell Biology, vol. 12, No. 9, pp. 777–783 (1993).

A. M. Cooper, Disseminated Tuberculosis in Interferon γ Gene–disrupted Mice, J. Exp. Med., vol. 178, pp. 2243–2247 (1993).

85A C1

GTCACCGTCCTTGAGATCACC ATG GAT GCA ATG AAG AGA GGG CTC TGC TGT GTG CTG CTG CTG TGT
                      Met Asp Ala Met Lys Arg Gly Leu Cys Cys Val Leu Leu Leu Cys

GGA GCA GTC TTC GTT TCG CCC AGC GAG ATC TTT TCC CGG CCG GGC TTG CCG GTG GAG TAC    (SEQ ID NO.26)
Gly Ala Val Phe Val Ser Pro Ser Glu Ile Phe Ser Arg Pro Gly Leu Pro Val Glu Tyr   (SEQ ID NO.27)

|———— tPA sig.seq. ————|—— tPA NH2 ter ——|········ AG 85 mature protein (NH2-ter)

85A C2

GTCACCGTCCTTGAGATCTACC ATG GGC TTT TCC CGG CCG GGC TTG CCG GTG GAG TAC    (SEQ ID NO.28)
                       Met Gly Phe Ser Arg Pro Gly Leu Pro Val Glu Tyr   (SEQ ID NO.29)
|—— Bgl II ——|

85A C3

CTGCAGTCACCGTCCTTGAGATCTACC ATG GCA CAG CTT GTT GAC AGG GTT CGT
                            Met Ala Gln Leu Val Asp Arg Val Arg

GGC GCC GTC ACG GGT ATG TCG CGT CGA CTC GTG GTC GGC GCC GCC CTA GTG
Gly Ala Val Thr Gly Met Ser Arg Arg Leu Val Val Gly Ala Val Gly Ala Ala Leu Val

TCG GGT CTG GTC GTC GGC GTC GGT GGC GTC GGG ACC GCG GCA TTT TCC CGG CGC    (SEQ ID NO.30)
Ser Gly Leu Val Val Gly Ala Val Gly Gly Thr Ala Gly Ala Phe Ser Arg Pro Gly   (SEQ ID NO.31)

CTGCAGTCACCGTCCTTGAGATCACCATG GAT GCA ATG AAG AGA GGG CTC TGC TGT GTG CTG CTG
⎯⎯⎯⎯⎯⎯⎯⎯⎯⎯⎯⎯⎯⎯⎯⎯⎯⎯⎯⎯⎯⎯⎯⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯
                                Met Asp Ala Met Lys Arg Gly Leu Cys Cys Val Leu Leu
                                ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯

CTG TGT GGA CCA GTC TTC GTT TCG CCC AGC GAG ATC TCC TTC TCC CGG CCG           (SEQ ID NO.32)
⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯
Leu Cys Gly Ala Val Phe Val Ser Pro Ser Glu Ile Ser Phe Ser Arg Pro          (SEQ ID NO.33)
⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯

85C C1

CTGCAGTCACCGTCCTTGAGATCACCATG GAT GCA ATG AAG AGA GGG CTC TGC TGT GTG CTG CTG
⎯⎯⎯⎯⎯⎯⎯⎯⎯⎯⎯⎯⎯⎯⎯⎯⎯⎯⎯⎯⎯⎯⎯⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯
                                Met Asp Ala Met Lys Arg Gly Leu Cys Cys Val Leu Leu

CTG TGT GGA GCA GTC TTC GTT TCG CCC AGC GAG ATC TCC TTC TCT AGG CCC          (SEQ ID NO.34)
Leu Cys Gly Ala Val Phe Val Ser Pro Ser Glu Ile Ser Phe Ser Arg Pro          (SEQ ID NO.35)

FIG.7B

POLYNUCLEOTIDE TUBERCULOSIS VACCINE

BACKGROUND OF THE INVENTION

A major obstacle to the development of vaccines against viruses and bacteria, particularly those with multiple serotypes or a high rate of mutation, against which elicitation of neutralizing antibodies and/or protective cell-mediated immune responses is desirable, is the diversity of the external proteins among different isolates or strains. Since cytotoxic T-lymphocytes (CTLs) in both mice and humans are capable of recognizing epitopes derived from conserved internal viral proteins [J. W. Yewdell et al., *Proc. Natl. Acad. Sci. (USA)* 82, 1785 (1985); A. R. M. Townsend, et al., *Cell* 44, 959 (1986); A. J. McMichael et al., *J. Gen. Virol.* 67, 719 (1986); J. Bastin et al., *J. Exp. Med.* 165, 1508 (1987); A. R. M. Townsend and H. Bodmer, *Annu. Rev. Immunol.* 7, 601 (1989)], and are thought to be important in the immune response against viruses [Y.-L. Lin and B. A. Askonas, *J. Exp. Med.* 154, 225 (1981); I. Gardner et al., *Eur. J. Immunol.* 4, 68 (1974); K. L. Yap and G. L. Ada, *Nature* 273, 238 (1978); A. J. McMichael et al., *New Engl. J. Med.* 309, 13 (1983); P. M. Taylor and B. A. Askonas, *Immunol.* 58, 417 (1986)], efforts have been directed towards the development of CTL vaccines capable of providing heterologous protection against different viral strains.

It is known that CTLs kill virally- or bacterially-infected cells when their T cell receptors recognize foreign peptides associated with MHC class I and/or class II molecules. These peptides can be derived from endogenously synthesized foreign proteins, regardless of the protein's location or function within the pathogen. By recognition of epitopes from conserved proteins, CTLs may provide heterologous protection. In the case of intracellular bacteria, proteins secreted by or released from the bacteria are processed and presented by MHC class I and II molecules, thereby generating T-cell responses that may play a role in reducing or eliminating infection.

Most efforts to generate CTL responses have either used replicating vectors to produce the protein antigen within the cell [J. R. Bennink et al., ibid. 311, 578 (1984); J. R. Bennink and J. W. Yewdell, *Curr. Top. Microbiol. Immunol.* 163, 153 (1990); C. K. Stover et al., *Nature* 351, 456 (1991); A. Aldovini and R. A. Young, *Nature* 351, 479 (1991); R. Schafer et al., *J. Immunol.* 149, 53 (1992); C. S. Hahn et al., *Proc. Natl. Acad. Sci. (USA)* 89, 2679 (1992)], or they have focused upon the introduction of peptides into the cytosol [F. R. Carbone and M. J. Bevan, *J. Exp. Med.* 169, 603 (1989); K. Deres et al., *Nature* 342, 561 (1989); H. Takahashi et al., ibid. 344, 873 (1990); D. S. Collins et al., *J. Immunol.* 148, 3336 (1992); M. J. Newman et al., ibid. 148, 2357 (1992)]. Both of these approaches have limitations that may reduce their utility as vaccines. Retroviral vectors have restrictions on the size and structure of polypeptides that can be expressed as fusion proteins while maintaining the ability of the recombinant virus to replicate [A.D. Miller, *Curr. Top. Microbiol. Immunol.* 158, 1 (1992)], and the effectiveness of vectors such as vaccinia for subsequent immunizations may be compromised by immune responses against vaccinia [E. L. Cooney et al., *Lancet* 337, 567 (1991)]. Also, viral vectors and modified pathogens have inherent risks that may hinder their use in humans [R. R. Redfield et al., *New Engl. J. Med.* 316, 673 (1987); L. Mascola et al., *Arch. Intern. Med.* 149, 1569 (1989)]. Furthermore, the selection of peptide epitopes to be presented is dependent upon the structure of an individual's MHC antigens and, therefore, peptide vaccines may have limited effectiveness due to the diversity of MHC haplotypes in outbred populations.

Benvenisty, N., and Reshef, L. [*PNAS* 83, 9551–9555, (1986)] showed that $CaCl_2$ precipitated DNA introduced into mice intraperitoneally (i.p.), intravenously (i.v.) or intramuscularly (i.m.) could be expressed. The intramuscular (i.m.) injection of DNA expression vectors in mice has been demonstrated to result in the uptake of DNA by the muscle cells and expression of the protein encoded by the DNA [J. A. Wolff et al., *Science* 247, 1465 (1990); G. Ascadi et al., *Nature* 352, 815 (1991)]. The plasmids were shown to be maintained episomally and did not replicate. Subsequently, persistent expression has been observed after i.m. injection in skeletal muscle of rats, fish and primates, and cardiac muscle of rats [H. Lin et al., *Circulation* 82, 2217 (1990); R. N. Kitsis et al., *Proc. Natl. Acad. Sci. (USA)* 88, 4138 (1991); E. Hansen et al., *FEBS Lett.* 290, 73 (1991); S. Jiao et al., *Hum. Gene Therapy* 3, 21 (1992); J. A. Wolff et al., *Human Mol. Genet.* 1, 363 (1992)]. The technique of using nucleic acids as therapeutic agents was reported in WO90/11092 (4 Oct. 1990), in which naked polynucleotides were used to vaccinate vertebrates.

Recently, the coordinate roles of B7 and the major histocompatibility complex (MHC) presentation of epitopes on the surface of antigen presenting cells in activating CTLs for the elimination of tumors was reviewed [Edgington, *Biotechnology* 11, 1117–1119, 1993]. Once the MHC molecule on the surface of an antigen presenting cell (APC) presents an epitope to a T-cell receptor (TCR), B7 expressed on the surface of the same APC acts as a second signal by binding to CTLA-4 or CD28. The result is rapid division of $CD4^+$ helper T-cells which signal $CD8^+$ T-cells to proliferate and kill the APC.

It is not necessary for the success of the method that immunization be intramuscular. Thus, Tang et al., [*Nature*, 356, 152–154 (1992)] disclosed that introduction of gold microprojectiles coated with DNA encoding bovine growth hormone (BGH) into the skin of mice resulted in production of anti-BGH antibodies in the mice. Furth et al., [*Analytical Biochemistry*, 205, 365–368, (1992)] showed that a jet injector could be used to transfect skin, muscle, fat, and mammary tissues of living animals. Various methods for introducing nucleic acids was recently reviewed [Friedman, T., *Science*, 244, 1275–1281 (1989)]. See also Robinson et al., [*Abstracts of Papers Presented at the 1992 meeting on Modern Approaches to New Vaccines, Including Prevention of AIDS*, Cold Spring Harbor, p 92; Vaccine 11, 957 (1993)], where the im, ip, and iv administration of avian influenza DNA into chickens was alleged to have provided protection against lethal challenge. Intravenous injection of a DNA-:cationic liposome complex in mice was shown by Zhu et al., [*Science* 261, 209–211 (9 Jul. 1993); see also WO93/24640, 9 Dec. 1993] to result in systemic expression of a cloned transgene. Recently, Ulmer et al., [*Science* 259, 1745–1749, (1993)] reported on the heterologous protection against influenza virus infection by injection of DNA encoding influenza virus proteins.

Wang et al., [*P.N.A.S. USA* 90, 4156–4160 (May, 1993)] reported on elicitation of immune responses in mice against HIV by intramuscular inoculation with a cloned, genomic (unspliced) HIV gene. However, the level of immune responses achieved was very low, and the system utilized portions of the mouse mammary tumor virus (MMTV) long terminal repeat (LTR) promoter and portions of the simian virus 40 (SV40) promoter and terminator. SV40 is known to transform cells, possibly through integration into host cellular DNA. Thus, the system described by Wang et al., is wholly inappropriate for administration to humans, which is one of the objects of the instant invention.

WO 93/17706 describes a method for vaccinating an animal against a virus, wherein carrier particles were coated with a gene construct and the coated particles are accelerated into cells of an animal.

Studies by Wolff et al. (supra) originally demonstrated that intramuscular injection of plasmid DNA encoding a reporter gene results in the expression of that gene in myocytes at and near the site of injection. Recent reports demonstrated the successful immunization of mice against influenza by the injection of plasmids encoding influenza A hemagglutinin (Montgomery, D. L. et al., 1993, Cell Biol., 12, pp. 777–783), or nucleoprotein (Montgomery, D. L. et al., supra; Ulmer, J. B. et al., 1993, Science, 259, pp. 1745–1749). The first use of DNA immunization for a herpes virus has been reported (Cox et al., 1993, J. Virol., 67, pp. 5664–5667). Injection of a plasmid encoding bovine herpesvirus 1 (BHV-1) glycoprotein g IV gave rise to anti-g IV antibodies in mice and calves. Upon intranasal challenge with BHV-1, immunized calves showed reduced symptoms and shed substantially less virus than controls.

Tuberculosis (TB) is a chronic infectious disease of the lung caused by the pathogen *Mycobacterium tuberculosis*. TB is one of the most clinically significant infections worldwide, with an incidence of 3 million deaths and 10 million new cases each year. It has been estimated that as much as one third of the world's population may be infected and, in developing countries, 55 million cases of active TB have been reported. Until the turn of the century, TB was the leading cause of death in the United States. But, with improved sanitary conditions and the advent of antimicrobial drugs, the incidence of mortality steadily declined to the point where it was predicted that the disease would be eradicated by the year 2000. However, in most developed countries, the number of cases of active TB has risen each year since the mid-1980's. Part of this resurgence has been attributed to immigration and the growing number of immunocompromised, HIV-infected individuals. If left unabated, it is predicted that TB will claim more than 30 million human lives in the next ten years. As alarming as these figures may seem, it is of even greater concern that multidrug-resistant (MDR) strains of *M. tuberculosis* have arisen. These MDR strains are not tractable by traditional drug therapy and have been responsible for several recent outbreaks of TB, particularly in urban centers. Therefore, one of the key components in the management of TB in the long-term will be an effective vaccine [for review see Bloom and Murray, 1993, Science 257, 1055].

*M. tuberculosis* is an intracellular pathogen that infects macrophages and is able to survive within the harsh environment of the phagolysosome in this type of cell. Most inhaled bacilli are destroyed by activated alveolar macrophages. However, the surviving bacilli can multiply in macrophages and be released upon cell death, which signals the infiltration of lymphocytes, monocytes and macrophages to the site. Lysis of the bacilli-laden macrophages is mediated by delayed-type hypersensitivity (DTH) and results in the development of a solid caseous tubercle surrounding the area of infected cells. Continued DTH causes the tubercle to liquefy, thereby releasing entrapped bacilli. The large dose of extracellular bacilli triggers further DTH, causing damage to the bronchi and dissemination by lymphatic, hematogenous and bronchial routes, and eventually allowing infectious bacilli to be spread by respiration.

Immunity to TB involves several types of effector cells. Activation of macrophages by cytokines, such as interferon-$\gamma$, is an effective means of minimizing intracellular mycobacterial multiplication. However, complete eradication of the bacilli by this means is often not achieved. Acquisition of protection against TB requires T lymphocytes. Among these, both $CD8^+$ and $CD4^+$ T cells seem to be important [Orme et al, 1993, J. Infect. Dis. 167, 1481]. These cell types secrete interferon-$\gamma$ in response to mycobacteria, indicative of a $T_h1$ immune response, and possess cytotoxic activity to mycobacteria-pulsed target cells. In recent studies using $\beta$-2 microglobulin- and CD8-deficient mice, CTL responses have been shown to be critical in providing protection against *M. tuberculosis* [Flynn et al, 1992, Proc. Natl. Acad. Sci. USA 89, 12013; Flynn et al, 1993, J. Exp. Med. 178, 2249; Cooper et al, 1993, J. Exp. Med. 178, 2243]. In contrast, B lymphocytes do not seem to be involved, and passive transfer of anti-mycobacterial antibodies does not provide protection. Therefore, effective vaccines against TB must generate cell-mediated immune responses.

Antigenic stimulation of T cells requires presentation by MHC molecules. In order for mycobacterial antigens to gain access to the antigen presentation pathway they must be released from the bacteria. In infected macrophages, this could be accomplished by secretion or bacterial lysis. Mycobacteria possess many potential T-cell antigens and several have now been identified [Andersen 1994, Dan. Med. Bull. 41, 205]. Some of these antigens are secreted by the bacteria. It is generally believed that immunity against TB is mediated by $CD8^+$ and $CD4^+$ T cells directed toward these secreted antigens. In mouse and guinea pig models of TB, protection from bacterial challenge, as measured by reduced weight loss, has been ,achieved using a mixture of secreted mycobacterial antigens [Pal and Horowitz, 1992 Infect. Immunity 60, 4781; Andersen 1994, Infect. Immunity 62, 2536; Collins, 1994, Veterin. Microbiol. 40, 95].

Several potentially protective T cell antigens have been identified in *M. tuberculosis* and some of these are being investigated as vaccine targets. Recent work has indicated that the predominant T-cell antigens are those proteins that are secreted by mycobacteria during their residence in macrophages, such as: i) the antigen 85 complex of proteins (85A, 85B, 85C) [Wiker and Harboe, 1992, Microbiol. Rev. 56, 648], ii) a 6 kDa protein termed ESAT-6 [Andersen 1994, Infect. Immunity 62, 2536], iii) a 38 kDa lipoprotein with homology to PhoS [Young and Garbe, 1991, Res. Microbiol. 142, 55; Andersen, 1992, J. Infect. Dis. 166, 874], iv) the 65 kDa GroEL heat-shock protein [Siva and Lowrie, 1994, Immunol. 82, 244], v) a 55 kDa protein rich in proline and threonine [Romain et al, 1993, Proc. Natl. Acad. Sci. USA 90, 5322], and vi) a 19 kDa lipoprotein [Faith et al, 1991, Immunol. 74, 1].

The genes for each of the three antigen 85 proteins (A, B, and C) have been cloned and sequenced [Borremans et al, 1989, Infect. Immunity 57, 3123; Content et al, Infect. Immunity 59, 3205; DeWit et al 1994, DNA Seq. 4, 267]. In addition, these structurally-related proteins are targets for strong T-cell responses after both infection and vaccination [Huygen et al, 1988, Scand. J. Immunol. 27, 187; Launois et al, 1991, Clin. Exp. Immunol. 86, 286; Huygen et al, 1992, Infect. Immunity 60, 2880; Munk et al, 1994, Infect. Immunity 62, 726; Launois et al, 1994, Infect. Immunity 62, 3679]. Therefore, the antigen 85 proteins are considered to be good vaccine targets.

SUMMARY OF THE INVENTION

To test the efficacy of DNA immunization in the prevention of *M.tb* disease, *M.tb* protein-coding DNA sequences were cloned into eukaryotic expression vectors. These DNA constructions elicit an immune response when injected into animals. Immunized animals are infected with mycobacteria to evaluate whether or not direct DNA immunization with the gene (or other *M.tb* genes) could protect them from disease. Nucleic acids, including DNA constructs and RNA transcripts, capable of inducing in vivo expression of *M.tb* proteins upon direct introduction into animal tissues via injection or otherwise are therefore disclosed. Injection of these nucleic acids may elicit immune responses which result in the production of cytotoxic T lymphocytes (CTLs) specific for *M.tb* antigens, as well as the generation of M.tb-specific helper T lymphocyte responses, which are protective upon subsequent challenge. These nucleic acids are useful as vaccines for inducing immunity to *M.tb*, which can prevent infection and/or ameliorate M.tb-related disease.

BRIEF DESCRIPTION OF THE DRAWINGS

FIG. 7A & B N-Terminal sequence verification of constructs is shown.

DETAILED DESCRIPTION OF THE INVENTION

Figure 1:
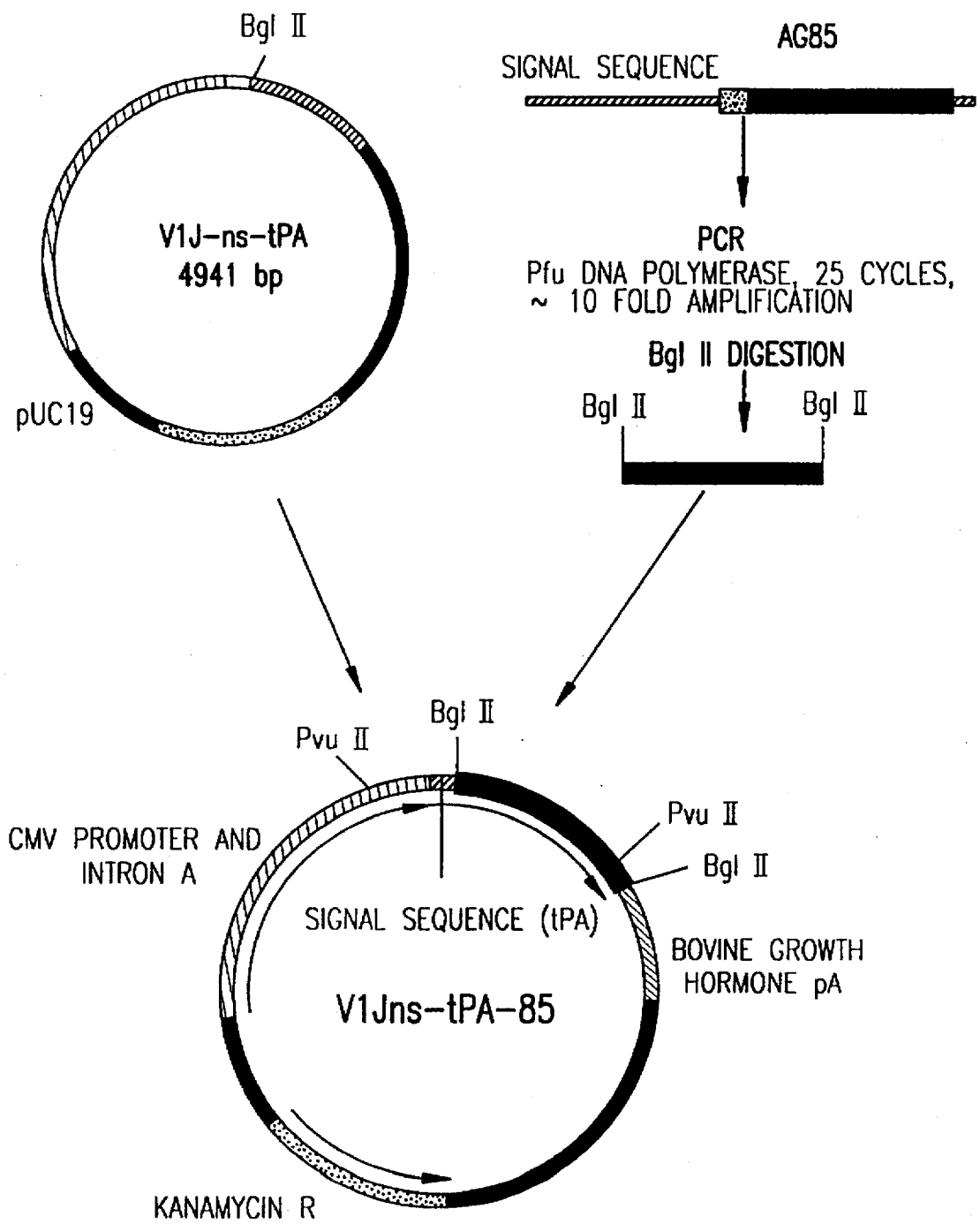
FIG. 1. General principle for cloning *M.tb* genes into expression vectors is shown.

This invention provides polynucleotides which, when directly introduced into a vertebrate in vivo, including mammals such as humans, induces the expression of encoded proteins within the animal. As used herein, a polynucleotide is a nucleic acid which contains essential regulatory elements such that upon introduction into a living vertebrate cell, and is able to direct the cellular machinery to produce translation products encoded by the genes comprising the polynucleotide. In one embodiment of the invention, the polynucleotide is a polydeoxyribonucleic acid comprising *Mycobacterium tuberculosis* (*M.tb*) genes operatively linked to a transcriptional promoter. In another embodiment of the invention the polynucleotide vaccine comprises polyribonucleic acid encoding *M.tb* genes which are amenable to translation by the eukaryotic cellular machinery (ribosomes, tRNAs, and other translation factors). Where the protein encoded by the polynucleotide is one which does not normally occur in that animal except in pathological conditions, (i.e. an heterologous protein) such as proteins associated with *M.tb*, the animals' immune system is activated to launch a protective immune response. Because these exogenous proteins are produced by the animals' own tissues, the expressed proteins are processed by the major histocompatibility system (MHC) in a fashion analogous to when an actual *M.tb* infection occurs. The result, as shown in this disclosure, is induction of immune responses against *M.tb*. Polynucleotides for the purpose of generating immune responses to an encoded protein are referred to herein as polynucleotide vaccines or PNV.

There are many embodiments of the instant invention which those skilled in the art can appreciate from the specification. Thus, different transcriptional promoters, terminators, carrier vectors or specific gene sequences may be used successfully.

The instant invention provides a method for using a polynucleotide which, upon introduction into mammalian tissue, induces the expression, in vivo, of the polynucleotide thereby producing the encoded protein. It is readily apparent to those skilled in the art that variations or derivatives of the nucleotide sequence encoding a protein can be produced which alter the amino acid sequence of the encoded protein. The altered expressed protein may have an altered amino acid sequence, yet still elicits immune responses which react with the mycobacterial protein, and are considered functional equivalents. In addition, fragments of the full length genes which encode portions of the full length protein may also be constructed. These fragments may encode a protein or peptide which elicits antibodies which react with the mycobacterial protein, and are considered functional equivalents.

In one embodiment of this invention, a gene encoding an *M.tb* gene product is incorporated in an expression vector. The vector contains a transcriptional promoter recognized by eukaryotic RNA polymerase, and a transcriptional terminator at the end of the *M.tb* gene coding sequence. In a preferred embodiment, the promoter is the cytomegalovirus promoter with the Intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator. The combination of CMVintA-BGH terminator is preferred. In addition, to assist in preparation of the polynucleotides in prokaryotic cells, an antibiotic resistance marker is also optionally included in the expression vector under transcriptional control of a suitable prokaryotic promoter. Ampicillin resistance genes, neomycin resistance genes or any other suitable antibiotic resistance marker may be used. In a preferred embodiment of this invention, the antibiotic resistance gene encodes a gene product for neomycin/kanamycin resistance. Further, to aid in the high level production of the polynucleotide by growth in prokaryotic organisms, it is advantageous for the vector to contain a prokaryotic origin of replication and be of high copy number. Any of a number of commercially available prokaryotic cloning vectors provide these elements. In a preferred embodiment of this invention, these functionalities are provided by the commercially available vectors known as the pUC series. It may be desirable, however, to remove non-essential DNA sequences. Thus, the lacZ and lacI coding sequences of pUC may be removed. It is also desirable that the vectors are not able to replicate in eukaryotic cells. This minimizes the risk of integration of polynucleotide vaccine sequences into the recipients' genome.

In another embodiment, the expression vector pnRSV is used, wherein the Rous sarcoma virus (RSV) long terminal repeat (LTR) is used as the promoter. In yet another embodiment, V1, a mutated pBR322 vector into which the CMV promoter and the BGH transcriptional terminator were cloned is used. In a preferred embodiment of this invention, the elements of V1 and pUC19 have been been combined to produce an expression vector named V1J.

Into V1J, V1JtPA or another desirable expression vector is cloned an *M.tb* gene, such as one of the antigen 85 complex genes, or any other *M.tb* gene which can induce anti-*M.tb* immune responses (CTLs, helper T lymphocytes and antibodies). In another embodiment, the ampicillin resistance gene is removed from V1J and replaced with a neomycin resistance gene, to generate V1J-neo, into which any of a number of different *M.tb* genes may be cloned for use according to this invention. In yet another embodiment, the vector is V1Jns, which is the same as V1Jneo except that a unique Sfi1 restriction site has been engineered into the single Kpn1 site at position 2114 of V1J-neo. The incidence of Sfi1 sites in human genomic DNA is very low (approximately 1 site per 100,000 bases). Thus, this vector allows careful monitoring for expression vector integration into host DNA, simply by Sfi1 digestion of extracted genomic DNA. In a further embodiment, the vector is V1R. In this vector, as much non-essential DNA as possible is "trimmed" to produce a highly compact vector. This vector allows larger inserts to be used, with less concern that undesirable sequences are encoded and optimizes uptake by cells when the construct encoding specific virus genes is introduced into surrounding tissue. The methods used in producing the foregoing vector modifications and development procedures may be accomplished according to methods known by those skilled in the art.

From this work those skilled in the art will recognize that one of the utilities of the instant invention is to provide a system for in vivo as well as in vitro testing and analysis so that a correlation of M.tb sequence diversity with CTL and T-cell proliferative responses, as well as other parameters can be made. The isolation and cloning of these various genes may be accomplished according to methods known to those skilled in the art. This invention further provides a method for systematic identification of *M.tb* strains and sequences for vaccine production. Incorporation of genes from primary isolates of M.tb strains provides an immunogen which induces immune responses against clinical isolates of the organism and thus meets a need as yet unmet in the field. Furthermore, if the virulent isolates change, the immunogen may be modified to reflect new sequences as necessary.

In one embodiment of this invention, a gene encoding an *M.tb* protein is directly linked to a transcriptional promoter. The use of tissue-specific promoters or enhancers, for example the muscle creatine kinase (MCK) enhancer element may be desirable to limit expression of the polynucleotide to a particular tissue type. For example, myocytes are terminally differentiated cells which do not divide. Integration of foreign DNA into chromosomes appears to require both cell division and protein synthesis. Thus, limiting protein expression to non-dividing cells such as myocytes may be preferable. However, use of the CMV promoter is adequate for achieving expression in many tissues into which the PNV is introduced.

*M.tb* and other genes are preferably ligated into an expression vector which has been specifically optimized for polynucleotide vaccinations. Elements include a transcriptional promoter, immunogenic epitopes, and additional cistrons encoding immunoenhancing or immunomodulatory genes, with their own promoters, transcriptional terminator, bacterial origin of replication and antibiotic resistance gene, as described herein. Optionally, the vector may contain internal ribosome entry sites (IRES) for the expression of polycistronic mRNA. Those skilled in the art will appreciate that RNA which has been transcribed in vitro to produce multicistronic mRNAs encoded by the DNA counterparts is within the scope of this invention. For this purpose, it is desirable to use as the transcriptional promoter such powerful RNA polymerase promoters as the T7 or SP6 promoters, and performing in vitro run-on transcription with a linearized DNA template. These methods are well known in the art.

The protective efficacy of polynucleotide *M.tb* immunogens against subsequent challenge is demonstrated by immunization with the DNA of this invention. This is advantageous since no infectious agent is involved, no assembly/replication of bacteria is required, and determinant selection is permitted. Furthermore, because the sequence of mycobacterial gene products may be conserved among various strains of *M.tb*, protection against subsequent challenge by another strain of *M.tb* is obtained.

The injection of a DNA expression vector encoding antigen 85A, B or C may result in the generation of significant protective immunity against subsequent challenge. In particular, specific CTLs and helper T lymphocyte responses may be produced.

Because each of the *M.tb* gene products exhibit a high degree of conservation among the various strains of *M.tb* and because immune responses may be generated in response to intracellular expression and MHC processing, it is expected that many different M.tb PNV constructs may give rise to cross reactive immune responses.

The invention offers a means to induce heterologous protective immunity without the need for self-replicating agents or adjuvants. The generation of high titer antibodies against expressed proteins after injection of viral protein and human growth hormone DNA, [Tang et al., *Nature* 356, 152, 1992], indicates this is a facile and highly effective means of making antibody-based vaccines, either separately or in combination with cytotoxic T-lymphocyte and helper T lymphocyte vaccines targeted towards conserved antigens.

The ease of producing and purifying DNA constructs compares favorably with traditional protein purification, facilitating the generation of combination vaccines. Thus, multiple constructs, for example encoding antigen 85 complex genes and any other *M.tb* gene also including non-*M.tb* genes may be prepared, mixed and co-administered. Additionally, protein expression is maintained following DNA injection [H. Lin et al., *Circulation* 82, 2217 (1990); R. N. Kitsis et al., *Proc. Natl. Acad. Sci.* (*USA*) 88, 4138 (1991); E. Hansen et al., *FEBS Lett.* 290, 73 (1991); S. Jiao et al., *Hum. Gene Therapy* 3, 21 (1992); J. A. Wolff et al., *Human Mol. Genet.* 1, 363 (1992)], the persistence of B- and T-cell memory may be enhanced [D. Gray and P. Matzinger, *J. Exp. Med.* 174, 969 (1991); S. Oehen et al., ibid. 176, 1273 (1992)], thereby engendering long-lived humoral and cell-mediated immunity.

The amount of expressible DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, an effective dose ranges of about 1 ng to 5 mg, 100 ng to 2.5 mg, 1 µg to 750 µg, and preferably about 10 µg to 300 µg of DNA is administered directly into muscle tissue. Subcutaneous injection, intradermal introduction, impression through the skin, and other modes of administration such as intraperitoneal, intravenous, or inhalation delivery are also suitable. It is also contemplated that booster vaccinations may be provided. Following vaccination with *M.tb* polynucleotide immunogen, boosting with *M.tb* protein immunogens such as the antigen 85 complex gene products is also contemplated. Parenteral administration, such as intravenous, intramuscular, subcutaneous or other means of administration of interleukin-12 protein (or other cytokines, e.g. GM-CSF), concurrently with or subsequent to parenteral introduction of the PNV of this invention may be advantageous.

The polynucleotide may be naked, that is, unassociated with any proteins, adjuvants or other agents which affect the recipients' immune system. In this case, it is desirable for the polycucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

In another embodiment, the invention is a polynucleotide which comprises contiguous nucleic acid sequences capable of being expressed to produce a gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an *M.tb* immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to insure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a $CD8^+$ response to NP that protected mice against challenge with heterologous strains of flu. (Montgomery, D. L. et al., supra; Ulmer, J. et al., supra)

There is strong evidence that cell-mediated immunity is important in controlling *M.tb* infection [Orme et al, 1993, J. Infect. Dis. 167, 1481; Cooper et al 1993, J. Exp. Med. 178, 2243; Flynn et al, 1993, J. Exp. Med. 178, 2249; Orme et al, 1993, J. Immunol. 151, 518]. Since DNA immunization can evoke both humoral and cell-mediated immune responses, its greatest advantage may be that it provides a relatively simple method to survey a large number of *M.tb* genes for their vaccine potential.

Immunization by DNA injection also allows, as discussed above, the ready assembly of multicomponent subunit vaccines. Simultaneous immunization with multiple influenza genes has recently been reported. (Donnelly, J. et al., 1994, Vaccines, pp 55–59). The inclusion in an *M.tb* vaccine of genes whose products activate different arms of the immune system may also provide thorough protection from s subsequent challenge.

The vaccines of the present invention are useful for administration to domesticated or agricultural animals, as well as humans. Vaccines of the present invention may be used to prevent and/or combat infection of any agricultural animals, including but not limited to, dairy cattle, which are susceptible to Mycobacterial infection. The techniques for administering these vaccines to animals and humans are known to those skilled in the veterinary and human health fields, respectively.

The following examples are provided to illustrate the present invention without, however, limiting the same thereto.

EXAMPLE 1

Vectors for Vaccine Production

A) V1 Expression Vector

The expression vector V1 was constructed from pCMVIE-AKI-DHFR [Y. Whang et al., *J. Virol.* 61, 1796 (1987)]. The AKI and DHFR genes were removed by cutting the vector with EcoR I and self-ligating. This vector does not contain intron A in the CMV promoter, so it was added as a PCR fragment that had a deleted internal Sac I site [at 1855 as numbered in B. S. Chapman et al., *Nuc. Acids Res.* 19, 3979 (1991)]. The template used for the PCR reactions was pCMVintA-Lux, made by ligating the Hind III and Nhe I fragment from pCMV6a120 [see B. S. Chapman et al., ibid.,] which includes hCMV-IE1 enhancer/promoter and intron A, into the Hind III and Xba I sites of pBL3 to generate pCMVIntBL. The 1881 base pair luciferase gene fragment (Hind III-Sma I Klenow filled-in) from RSV-Lux [J. R. de Wet et al., *Mol. Cell Biol.* 7, 725, 1987] was cloned into the Sal I site of pCMVIntBL, which was Klenow filled-in and phosphatase treated.

The primers that spanned intron A are:

5' primer, SEQ. ID:1: 5'-CTATATAAGCAGAG CTCGTTTAG-3';

The 3' primer, SEQ ID:2: 5'-GTAGCAAAGATCTAAGGACG-GTGA CTGCAG-3'.

The primers used to remove the Sac I site are:

sense primer, SEQ ID:3: 5-GTATGTGTCTGAAAATGAGCGTG-

GAGATTGGGCTCGCAC-3' and the antisense primer, SEQ ID:4: 5'-GTGCGAGCCCAATCTC-CACGCTCATTTTCAGACACA TAC-3'.

The PCR fragment was cut with Sac I and Bgl II and inserted into the vector which had been cut with the same enzymes.

B) V1J Expression Vector

The purpose in creating V1J was to remove the promoter and transcription termination elements from vector V1 in order to place them within a more defined context, create a more compact vector, and to improve plasmid purification yields.

V1J is derived from vectors V1 and pUC18, a commercially available plasmid. V1 was digested with SspI and EcoRI restriction enzymes producing two fragments of DNA. The smaller of these fragments, containing the CMVintA promoter and Bovine Growth Hormone (BGH) transcription termination elements which control the expression of heterologous genes, was purified from an agarose electrophoresis gel. The ends of this DNA fragment were then "blunted" using the T4 DNA polymerase enzyme in order to facilitate its ligation to another "blunt-ended" DNA fragment.

pUC18 was chosen to provide the "backbone" of the expression vector. It is known to produce high yields of plasmid, is well-characterized by sequence and function, and is of small size. The entire lac operon was removed from this vector by partial digestion with the HaeII restriction enzyme. The remaining plasmid was purified from an agarose electrophoresis gel, blunt-ended with the T4 DNA polymerase treated with calf intestinal alkaline phosphatase, and ligated to the CMVintA/BGH element described above. Plasmids exhibiting either of two possible orientations of the promoter elements within the pUC backbone were obtained. One of these plasmids gave much higher yields of DNA in *E. coli* and was designated V1J. This vector's structure was verified by sequence analysis of the junction regions and was subsequently demonstrated to give comparable or higher expression of heterologous genes compared with V1.

C) V1Jneo Expression Vector

It was necessary to remove the amp$^r$ gene used for antibiotic selection of bacteria harboring V1J because ampicillin may not be desirable in large-scale fermenters. The amp$^r$ gene from the pUC backbone of V1J was removed by digestion with SspI and Eam1105I restriction enzymes. The remaining plasmid was purified by agarose gel electrophoresis, blunt-ended with T4 DNA polymerase, and then treated with calf intestinal alkaline phosphatase. The commercially available kan$^r$ gene, derived from transposon 903 and contained within the pUC4K plasmid, was excised using the PstI restriction enzyme, purified by agarose gel electrophoresis, and blunt-ended with T4 DNA polymerase. This fragment was ligated with the V1J backbone and plasmids with the kan$^r$ gene in either orientation were derived which were designated as V1Jneo #'s 1 and 3. Each of these plasmids was confirmed by restriction enzyme digestion analysis, DNA sequencing of the junction regions, and was shown to produce similar quantities of plasmid as V1J. Expression of heterologous gene products was also comparable to V1J for these V1Jneo vectors. V1Jneo#3, referred to as V1Jneo hereafter, was selected which contains the kan$^r$ gene in the same orientation as the amp$^r$ gene in V1J as the expression construct.

D) V1Jns Expression Vector

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

E) V1Jns-tPA

In order to provide an heterologous leader peptide sequence to secreted and/or membrane proteins, V1Jns was modified to include the human tissue-specific plasminogen activator (tPA) leader. Two synthetic complementary oligomers were annealed and then ligated into V1Jn which had been BglII digested. The sense and antisense oligomers were 5'-GATC ACC ATG GAT GCA ATG AAG AGA GGG CTC TGC TGT GTG CTG CTG CTG TGT GGA GCA GTC TTC GTT TCG CCC AGC CA-3', SEQ. ID:5:, and 5'-GAT CTC GCT GGG CGA AAC GAA GAC TGC TCC ACA CAG CAG CAG CAC ACA GCA GAG CCC TCT CTT CAT TGC ATC CAT GGT-3', SEQ. ID:6. The Kozak sequence is underlined in the sense oligomer. These oligomers have overhanging bases compatible for ligation to BglII-cleaved sequences. After ligation the upstream BglII site is destroyed while the downstream BglII is retained for subsequent ligations. Both the junction sites as well as the entire tPA leader sequence were verified by DNA sequencing. Additionally, in order to conform with the consensus optimized vector V1Jns (=V1Jneo with an SfiI site), an SfiI restriction site was placed at the KpnI site within the BGH terminator region of V1Jn-tPA by blunting the KpnI site with T4 DNA polymerase followed by ligation with an SfiI linker (catalogue #1138, New England Biolabs). This modification was verified by restriction digestion and agarose gel electrophoresis.

F) pGEM-3-X-IRES-B7

(where X=any antigenic gene) As an example of a dicistronic vaccine construct which provides coordinate expression of a gene encoding an immunogen and a gene encoding an immunostimulatory protein, the murine B7 gene was PCR amplified from the B lymphoma cell line CH1 (obtained from the ATCC). B7 is a member of a family of proteins which provide essential costimulation T cell activation by antigen in the context of major histocompatibility complexes I and II. CH1 cells provide a good source of B7 mRNA because they have the phenotype of being constitutively activated and B7 is expressed primarily by activated antigen presenting cells such as B cells and macrophages. These cells were further stimulated in vitro using cAMP or IL-4 and mRNA prepared using standard guanidinium thiocyanate procedures. cDNA synthesis was performed using this mRNA using the. GeneAmp RNA PCR kit (Perkin-Elmer Cetus) and a priming oligomer (5'-GTA CCT CAT GAG CCA CAT AAT ACC ATG-3', SEQ. ID:7:) specific for B7 located downstream of the B7 translational open reading frame. B7 was amplified by PCR using the following sense and antisense PCR oligomers: 5'-GGT ACA AGA TCT ACC ATG GCT TGC AAT TGT CAG TTG ATG C-3', SEQ. ID:8:, and 5'-CCA CAT AGA TCT CCA TGG GAA CTA AAG GAA GAC GGT CTG TTC-3', SEQ. ID:9:, respectively. These oligomers provide BglII restriction enzyme sites at the ends of the insert as well as a Kozak translation initiation sequence containing an NcoI restriction site and an additional NcoI site located immediately prior to the 3'-terminal BglII site. NcoI digestion yielded a fragment suitable for cloning into pGEM-3-IRES which had been digested with NcoI. The resulting vector, pGEM-3-IRES-B7, contains an IRES-B7 cassette which can easily be transferred to V1Jns-X, where X represents an antigen-encoding gene.

G) pGEM-3-X-IRES-GM-CSF (where X=any antigenic gene) This vector contains a cassette analogous to that described in item C above except that the gene for the immunostimulatory cytokine, GM-CSF, is used rather than B7. GM-CSF is a macrophage differentiation and stimulation cytokine which has been shown to elicit potent anti-tumor T cell activities in vivo [G. Dranoff et al., *Proc. Natl. Acad. Sci. USA*, 90, 3539 (1993)].

H) pGEM-3-X-IRES-IL-12

(where X=any antigenic gene) This vector contains a cassette analogous to that described in item C above except that the gene for the immunostimulatory cytokine, IL-12, is used rather than B7. IL-12 has been demonstrated to have an influential role in shifting immune responses towards cellular, T cell-dominated pathways as opposed to humoral responses [L. Alfonso et al., *Science*, 263, 235, 1994].

EXAMPLE 2

Vector V1R Preparation

In an effort to continue to optimize the basic vaccination vector, a derivative of V1Jns, designated V1R, was prepared. The purpose for this vector construction was to obtain a minimum-sized vaccine vector without unneeded DNA sequences, which still retained the overall optimized heterologous gene expression characteristics and high plasmid yields that V1J and V1Jns afford. It was determined from the literature as well as by experiment that (1) regions within the pUC backbone comprising the *E. coli* origin of replication could be removed without affecting plasmid yield from bacteria; (2) the 3'-region of the kan$^r$ gene following the kanamycin open reading frame could be removed if a bacterial terminator was inserted in its place; and, (3) ~300 bp from the 3'-half of the BGH terminator could be removed without affecting its regulatory function (following the original KpnI restriction enzyme site within the BGH element).

V1R was constructed by using PCR to synthesize three segments of DNA from V1Jns representing the CMVintA promoter/BGH terminator, origin of replication, and kanamycin resistance elements, respectively. Restriction enzymes unique for each segment were added to each segment end using the PCR oligomers: SspI and XhoI for CMVintA/BGH; EcoRV and BamHI for the kan$^r$ gene; and, BclI and SalI for the ori$^r$. These enzyme sites were chosen because they allow directional ligation of each of the PCR-derived DNA segments with subsequent loss of each site: EcoRV and SspI leave blunt-ended DNAs which are compatible for ligation while BamHI and BclI leave complementary overhangs as do SalI and XhoI. After obtaining these segments by PCR each segment was digested with the appropriate restriction enzymes indicated above and then ligated together in a single reaction mixture containing all three DNA segments. The 5'-end of the ori$^r$ was designed to include the T2 rho independent terminator sequence that is normally found in this region so that it could provide termination information for the kanamycin resistance gene. The ligated product was confirmed by restriction enzyme digestion (>8 enzymes) as well as by DNA sequencing of the ligation junctions. DNA plasmid yields and heterologous expression using viral genes within V1R appear similar to V1Jns. The net reduction in vector size achieved was 1346 bp (V1Jns=4.86 kb; V1R=3.52 kb).

PCR oligomer sequences used to synthesize V1R (restriction enzyme sites are underlined and identified in brackets following sequence):

5'-GGT ACA AAT ATT GG CTA TTG GCC ATT GCA TAC G-3' [SspI], SEQ.ID:10:, (1)

5'-CCA CAT CTC GAG GAA CCG GGT CAA TTC TTC AGC ACC-3' [XhoI], SEQ.ID:11: (2)

(for CMVintA/BGH segment)

5'-GGT ACA GAT ATC GGA AAG CCA CGT TGT GTC TCA AAA TC-3'[EcoRV], SEQ.ID:12: (3)

5'-CCA CAT GGA TCC G TAA TGC TCT GCC ACT GTT ACA ACC-3' [BamHI], SEQ.ID:13: (4)

(for kanamycin resistance gene segment)

5'-GGT ACA TGA TCA CGT AGA AAA GAT CAA AGG ATC TTC TTG-3'[BclI], SEQ.ID:14:, (5)

5'-CCA CAT GTC GAC CC GTA AAA AGG CCG CGT TGC TGG-3'[SalI], SEQ.ID:15: (6)

(for *E. coli* origin of replication)

EXAMPLE 3

Cell Culture and Transfection

For preparation of stably transfected cell lines expressing M.tb antigens RD cells (human rhabdomyosarcoma ATCC CCL 136) were grown at 37° C., 5% $CO_2$ in Dulbecco's modified Eagle's medium (DMEM) supplemented with 10% heat inactivated fetal bovine serum, 20 mM HEPES, 4 mM L-glutamine, and 100 μg/mL each of penicillin and streptomycin. Cells were seeded at $1.5\times10^6$ cells/100 $mm^2$ plate and grown for 18 hours. Cell were transfected with 10 μg/plate of the TB construct and 10 μg of co-transfected Cat construct using the CellPhect kit (Pharmacia), and glycerol shocked (15% glycerol in PBS, pH 7.2 for 2.5 min) 5 hours after DNA was added to the cells. Cultures were harvested 72 hours after transfection by washing the plates 2×-10 mL of cold PBS, pH 7.2, adding 5 mL of cold TEN buffer (40 mM TRIS-Cl, pH 7.5, 1 mM EDTA, 150 mM NaCl) and scraping. For analysis of protein expression, cell pellets were lysed in 50 μL of Single Detergent Lysis Buffer (50 mM Tris-Cl, pH 8.0, 150 mM NaCl, 0.02% NAN3, 1% Nonidet P-40, 100 mM PMSF, 2 μg/mL aprotinin, 2 μg/mL leupeptin, and 1 μg/mL Pepstatin A) and sonicated on ice (2–15 second bursts). Lysates were centrifuged at 13,000×g, 4° C., for 10 minutes. Protein concentration was determined by the Bradford method and 20 μg of cell extract protein per lane was applied to a 10% TRIS-glycine polyacrylamide gel (Novex), then transferred to Immobilon P (Millipore) membrane. Immunoblots were reacted overnight with a 1:20 dilution of the mouse monoclonal antibody TD 17-4 [Huygen et al, 1994, Infect. Immunity 62, 363], followed by a 1.5 hours reaction with a 1:1000 dilution of goat anti-mouse IgGFc peroxidase (Jackson). The blots were developed using the ECL kit (Amersham).

EXAMPLE 4

Cloning and DNA Preparation

1. Construction of V1Jns-tPA-85A (contains mature Ag85A with tPA signal sequence) was done using the following primers:

sense 85A.C1 primer [SEQ.ID.NO.:16] GG AAG ATC TTT TCC CGG CCG GGC TTG CCG Bgl II antisense 85A primer [SEQ.ID.NO.:17] GGAAGATCTTGTCTGTTCGGAGCTAGGC.

Figure 2:
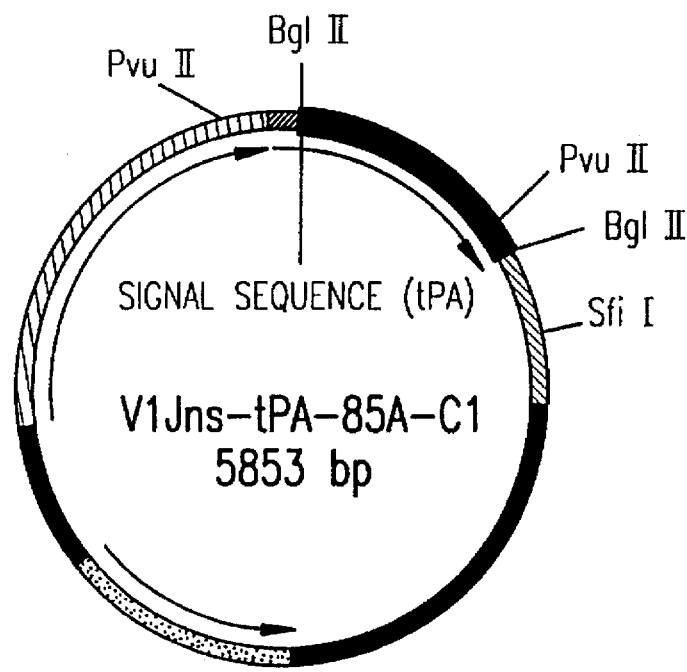
FIG. 2. Vector map of V1Jns.tPA85A.C1 is shown.
Figure 3:
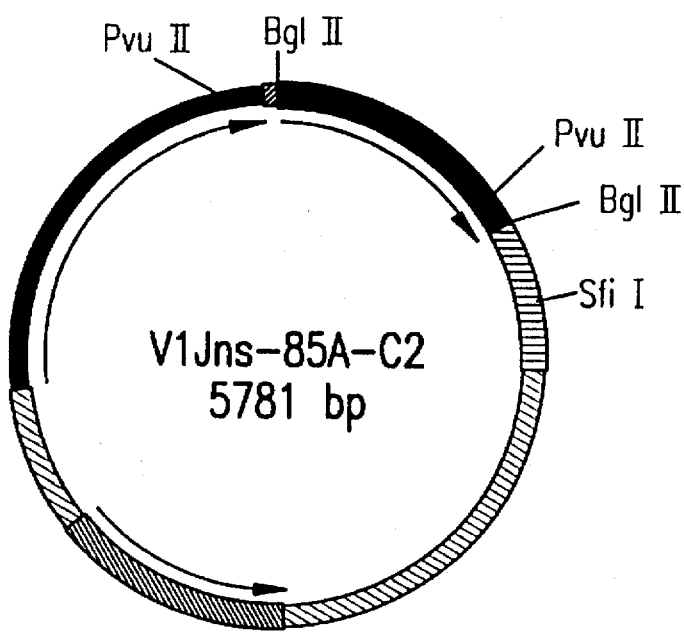
FIG. 3. Vector map of V1Jns.85A.C2 is shown.
Figure 4:
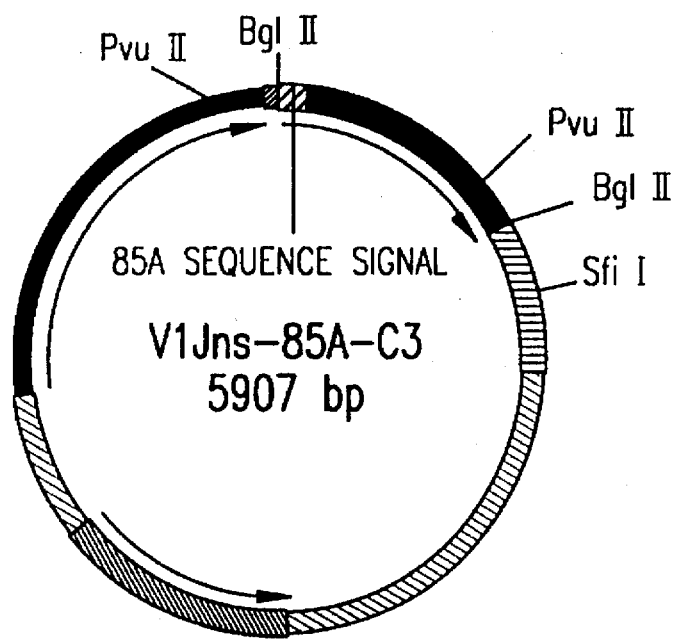
FIG. 4. Vector map of V1Jns.85A.C3 is shown.
Figure 5:
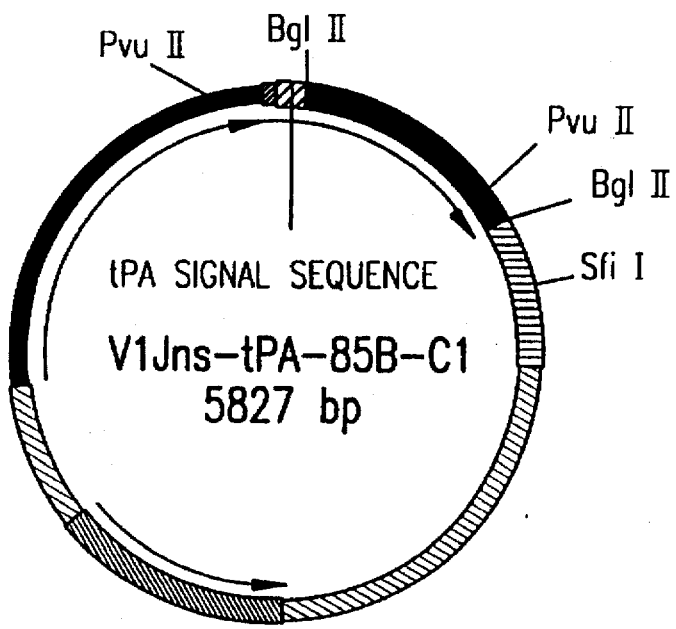
FIG. 5. Vector map of V1Jns.tPA85B.C1 is shown.
Figure 6:
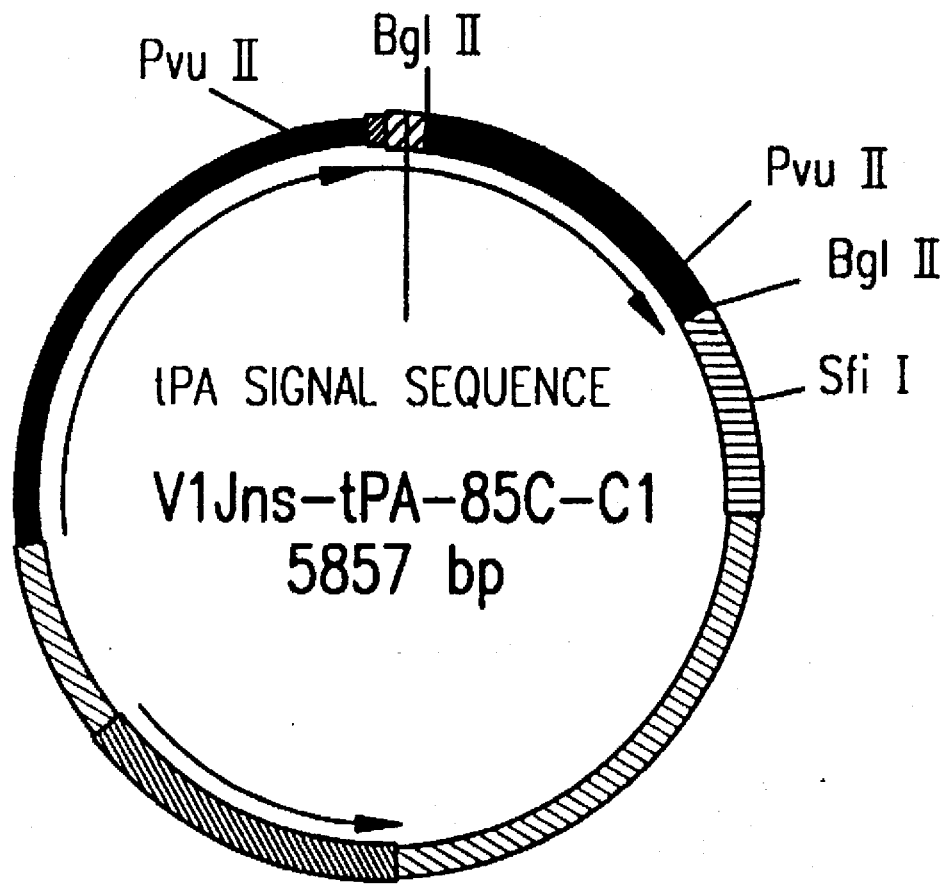
FIG. 6. Vector map of V1Jns.tPA85C.C1 is shown.

The Ag85A from *M. tuberculosis* was amplified from plasmid p85A.tub, which was prepared by ligating an 800 bp HindIII fragment to a 1600 bp HindIII-SphI fragment from FIG. 2 of Borremans et al, 1989 [Infect. Immunity 57, 3123]. The resulting 2400 bp insert was subcloned in the HindIII and SphI sites of the BlueScribe M13+. The entire coding sequence and flanking regions in BlueScribe M13+ (VCS/Stratagene) were amplified by PCR with the indicated primers in the following conditions. Each 100 µl reaction contains 2.5 Units Cloned Pfu DNA Polymerase (Stratagene), 200 mM dNTP, 0.5 µg of each primer and 250 ng of template DNA in the reaction buffer supplied with the enzyme (Stratagene). The Hybaid Thermal Reactor was programmed as follows: 5 minutes denaturation at 94° C. followed by 25 cycles (1 minute at 94° C., 2 minutes at 55° C. and 3 minutes at 72° C.) ending with 10 minutes extension at 72° C.

Amplified DNA was digested with 50 µg/ml Proteinase K (Boehringer Mannheim) for 30 minutes at 37° C., heated 10 minutes at 95° C. followed by 2 phenol (Chloroform-Isoamyl alcohol) extractions and precipitated with 1 volume of isopropanol, washed twice with 70% ethanol, dried and dissolved in 20 µl $H_2O$. 3 µg of amplified DNA was digested with 40 Units of Bgl II (Boehringer Mannheim) and the 907 bp fragment (in the case of 85A-C1) was isolated on a 1% agarose gel and extracted on "Prep a Gene" (BioRad) following the manufacturer's instructions.

Fifty ng of this fragment was ligated to 20 ng of the Bgl II is digested and dephosphorylated V1Jns.tPA vector in a 10 µl reaction containing 2.5 Units T4 DNA ligase (Amersham) in ligation buffer for 16 hours at 14° C., transformed into competent DH5 *E. coli* (BRL) and plated on Kanamycin (50 µg/ml) containing LB Agar medium. Transformants were picked up and their plasmidic DNA was restricted with Bgl II (to confirm the presence of insert) and with Pvu II to define its orientation.

2. Construction of V1Jns-85A [C2] (contains mature Ag85A with no signal sequence) was done using the following primers:

Sense 85A C2 [SEQ.ID.NO.:18] GGAAGATCTACC ATG GGC TTT TCC CGG CCG GGC TTG C

Antisense 85A [SEQ.ID.NO.:17] GGAAGATCTTGCTGTTCG-GAGCTAGGC.

The same procedure as 1 above was followed, except that cloning was in V1Jns.

3. Construction of V1Jns-85A [C3] (contains Ag85A with its own signal sequence) was done using the primers:

Sense 85A C3 [SEQ.ID.NO.:19] GGAAGATCTACC ATG GCA CAG CTT GTT GAC AGG GTT

Antisense 85A [SEQ.ID.NO.:17] GGAAGATCTTGCTGTTCG-GAGCTAGGC.

The same procedure as 1 above was followed, except that cloning was in V1Jns.

4. Construction of V1Jns-tPA-85B [C1] (contains Ag85B with tPA signal sequence) was done using the following primers:

Sense 85B [C1][SEQ.ID.NO.:20] GGAAG ATC TCC TTC TCC CGG CCG GGG CTG CCG GTC GAG

Antisense 85B [SEQ.ID.NO.:21] GGAAGATCTAACCTTCGGT-TGATCCCGTCAGCC.

The same procedure as 1 above was followed, except that the template for PCR was p85B.tub.

5. Construction of V1Jns-tPA-85C [C1] (contains Ag85C with tPA signal sequence) was done using the following primers:

Sense 85C [C1][SEQ.ID.NO.:22] GGAAG ATC TCC TTC TCT AGG CCC GGT CTT CCA

Antisense 85C [SEQ.ID.NO.:23] GGAAGATCTTGCCGAT-GCTGGCTTGCTGGCTCAGGC.

The same procedure as 1 above was followed, except that the template for PCR was p85C.tub.

6. Construction of V1Jns-85B [C2] (contains Ag85B with no signal sequence) is done using the following primers:

Sense 85B [C2][SEQ.ID.NO.:24] GGA AGA TCT ACC ATG GGC TTC TCC CGG CCG GGG CTG C

Antisense 85B [SEQ.ID.NO.:21] GGAAGATCTAACCTCGGT-TGATCCCGTCAGCC.

The same procedure as 1 above is followed, except that template for PCR is p85B.tub and that cloning is in V1Jns.

7. Construction of V1Jns-85C [C2] (contains Ag85C with no signal sequence) is done using the following primers:

Sense 85C [C2][SEQ.ID.NO.:25] GGA AGA TCT ACC ATG GGC TTC TCT AGG CCC GGT CTT C

Antisense 85C [SEQ.ID.NO.:23] GGAAGATCTTGCCGAT-GCTGGCTTGCTGGCTCAGGC.

The same procedure as 1 above is followed, except that template for PCR is p85C.tub and that cloning is in V1Jns.

After restriction analysis all of the constructions are partially sequenced across the vector junctions. Large scale DNA preparation was essentially as described (Montgomery, D. L. et al., supra).

The plasmid constructions were characterized by restriction mapping and sequence analysis of the vector-insert junctions (see FIGS. 1–6). Results were consistent with published *M.tb* sequence data and showed that the initiation codon was intact for each construct (FIG. 7). Also shown are the various additional amino acid residues unrelated to *M.tb* Ag85 that were inserted as a result of cloning.

EXAMPLE 5

Expression of *M.tb* Proteins from V1Jns.tPA Plasmids

Rhabdomyosarcoma cells (ATCC CCL136) were planted one day before use at a density of $1.2 \times 10^6$ cells per 9.5 cm² well in six-well tissue culture clusters in high glucose DMEM supplemented with 10% heat-inactivated fetal calf serum, 2 mM L-glutamine, 25 mM HEPES, 50 U/ml penicillin and 50 µg/ml streptomycin. (All from BRL-Gibco) Phenol: chloroform extracted cesium chloride purified plasmid DNA was precipitated with calcium phosphate using Pharmacia CellPhect reagents according to the kit instructions except that 5–15 µg is used for each 9.5 cm² well of RD cells. Cultures were glycerol shocked six hours post addition of calcium phosphate-DNA precipate; after refeeding, cultures were incubated for two days prior to harvest.

Lysates of transfected cultures were prepared in 1X RIPA (0.5% SDS, 1.0% TRITON X-100, 1% sodium deoxycholate, 1 mM EDTA, 150 mM NaCl, 25 mM TRIS-HCl pH 7.4) supplemented with 1 µM leupeptin, 1 µM pepstatin, 300 nM aprotinin, and 10 µM TLCK, and sonicated briefly to reduce viscosity. Lysates were resolved by electrophoresis on 10% Tricine gels (Novex) and then transferred to nitrocellulose membranes. Immunoblots were processed with M.tb, monoclonal antibodies 17/4 and 32/15 [Huygen et al, 1994, Infect. Immunity 62, 363] and developed with the ECL detection kit (Amersham).

Figure 8:
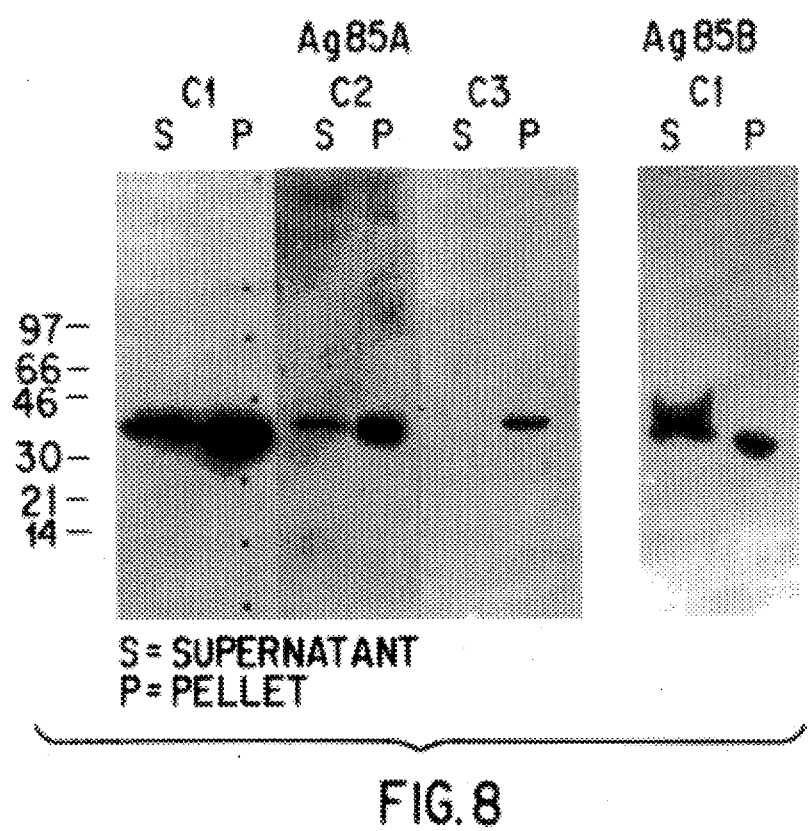
FIG. 8 Expression of *M.tb* proteins in tissue culture is shown.

Expression of M.tb antigen 85 complex genes was demonstrated by transient transfection of RD cells. Lysates of transfected or mock transfected cells were fractionated by SDS PAGE and analyzed by immunoblotting. FIG. 8 shows that V1Jns.tPA-85A(C1), V1Jns.tPA-85A(C2), V1Jns.tPA-85A(C3), and V1Jns.tPA-85B(C1) transfected RD cells express an immunoreactive protein with an apparent molecular weight of approximately 30–32 kDa.

EXAMPLE 6

Immunization with PNV and Expression of Antigen 85 Proteins In Vivo

Figure 9A:
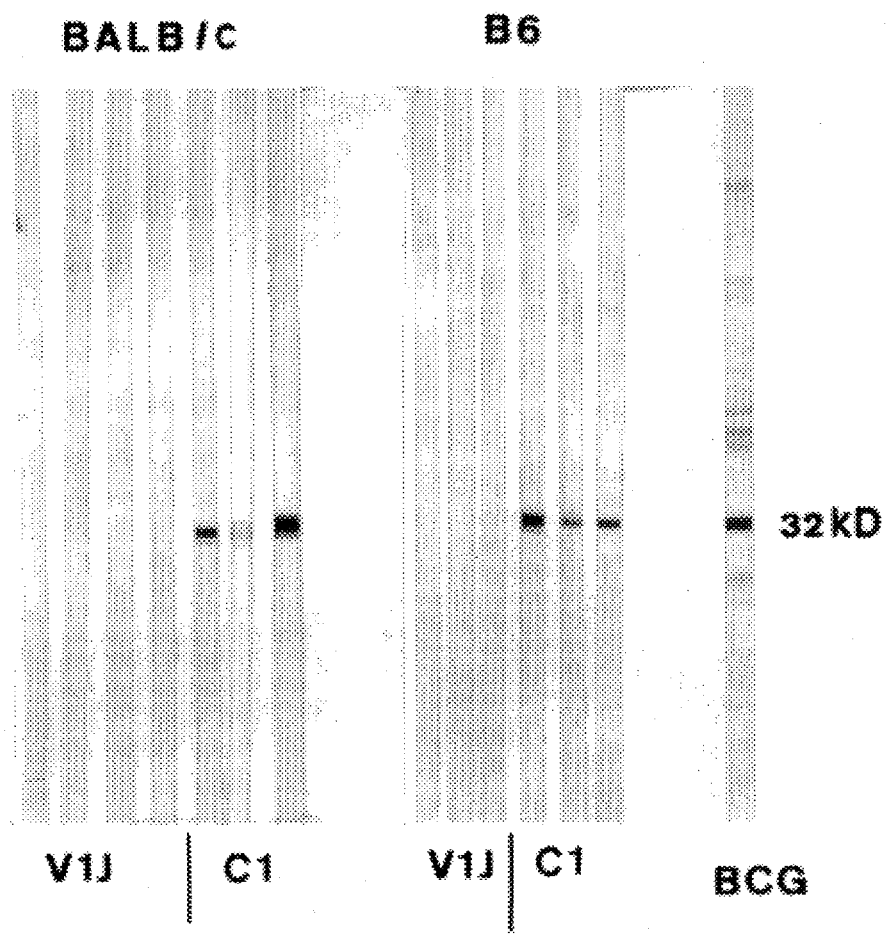
FIG. 9A & B Production of antigen 85A-specific antibodies in DNA-vaccinated mice is shown.
Figure 9B:
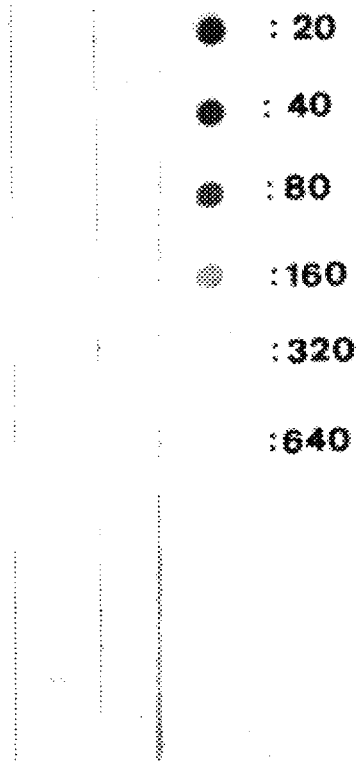
Figure 10:
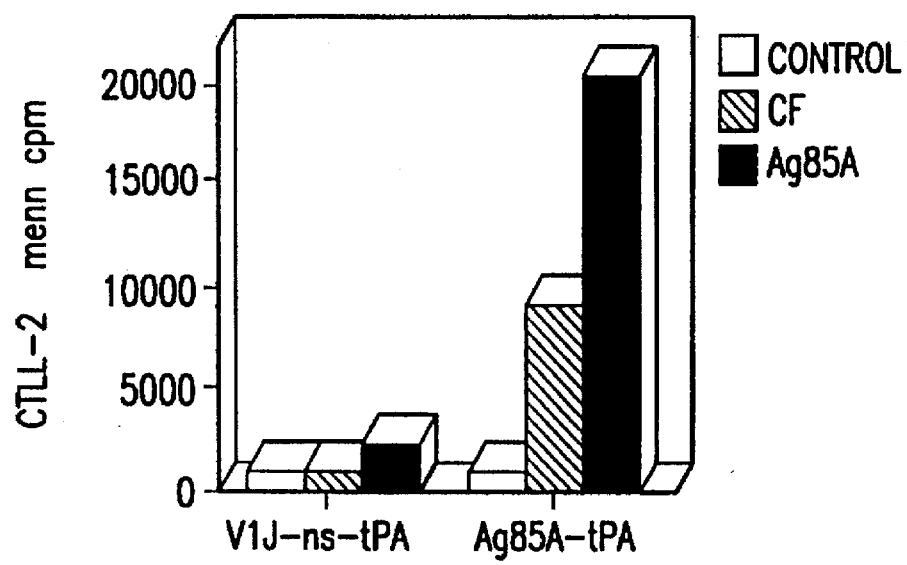
FIG. 10 IL-2 production in BALB/c mice by a Tb DNA vaccine is shown.
Figure 11:
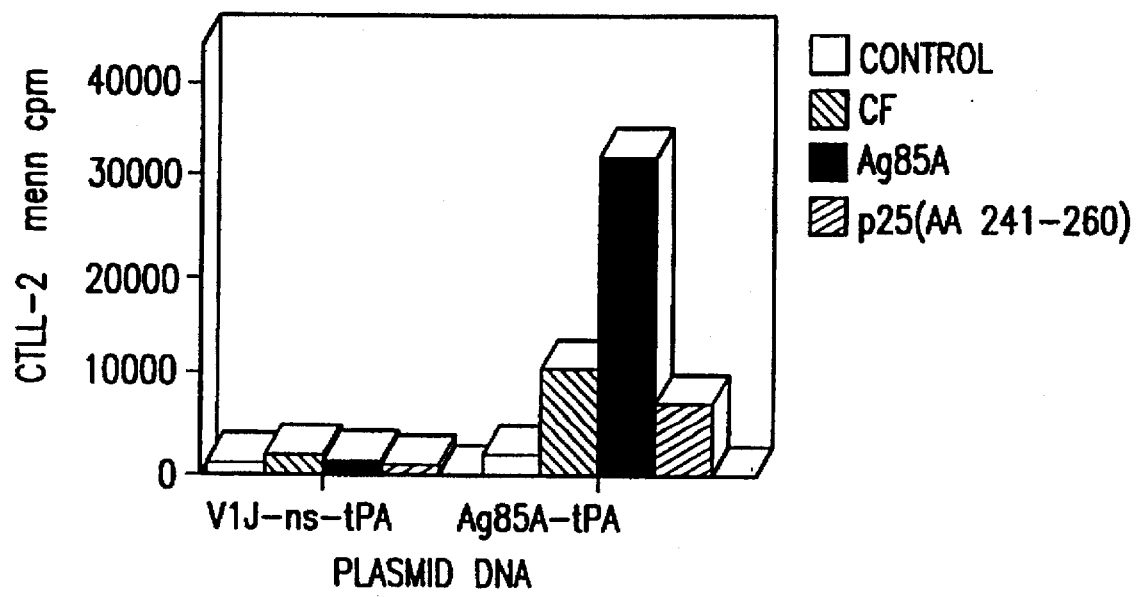
FIG. 11 IL-2 production in C57BL/6 mice by a Tb DNA vaccine is shown.
Figure 12:
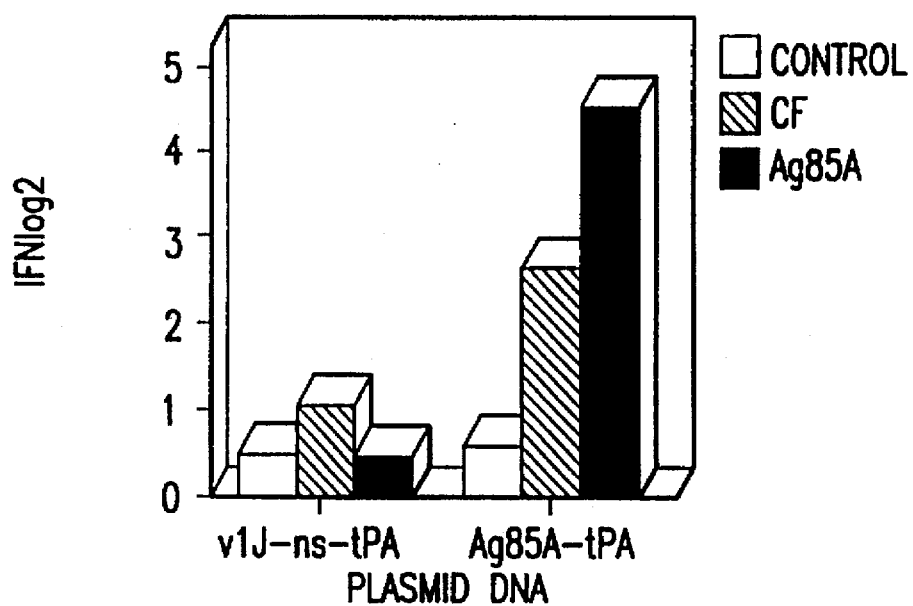
FIG. 12 IFN-γ production in BALB/c mice by a Tb DNA vaccine is shown.

Five- to six-week-old female BALB/c and C57BL/6 mice were anesthetized by intraperitoneal (i.p.) injection of a mixture of 5 mg ketamine HCl (Aveco, Fort Dodge, Iowa) and 0.5 mg xylazine (Mobley Corp., Shawnee, Kans.) in saline. The hind legs were washed with 70% ethanol. Animals were injected three times with 100 µl of DNA (2 mg/ml) suspended in saline: 50 µl each leg. At 17–18 days after immunization, serum samples were collected and analyzed for the presence of anti-Ag85 antibodies. FIG. 9 shows specific immunoblot reactivity of sera from Ag85 DNA-injected mice (C1) but not from mice that received a control DNA not containing a gene insert (V1J). Reactivity was detected to a serum dilution of at least 1:160 against 300 ng of purified antigen 85A (FIG. 9b). This demonstrates that injection of Ag85 DNA resulted in Ag85 expression in vivo such that it was available for the generation of antibody responses in both BALB/c and C57BL/6 (B6) mice.

EXAMPLE 7

Antigen 85-Specific T-Cell Responses

Figure 13:
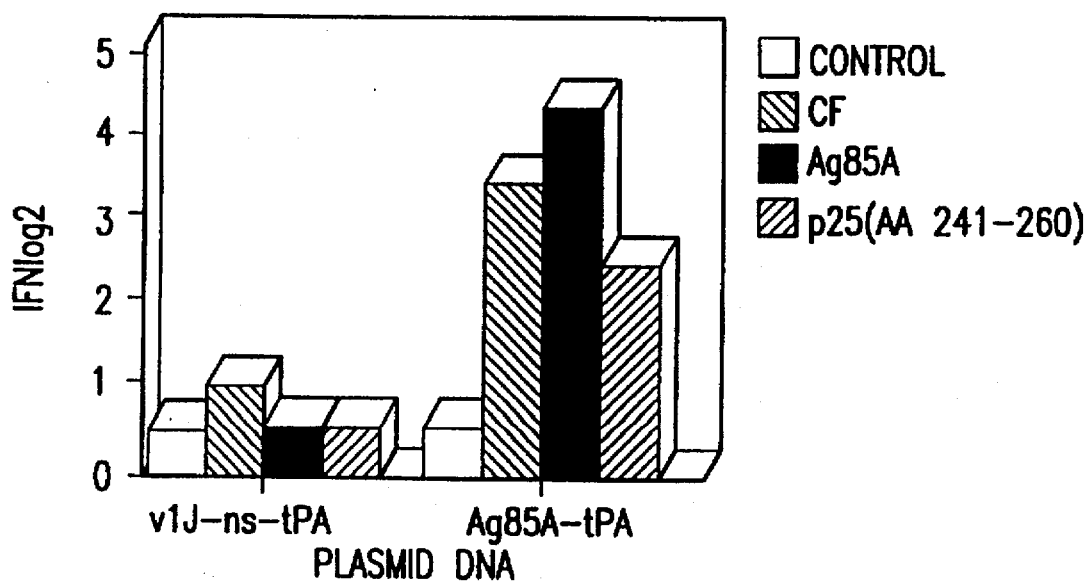
FIG. 13 IFN-γ production in C57BL/6 mice by a Tb DNA vaccine is shown.
Figure 14:
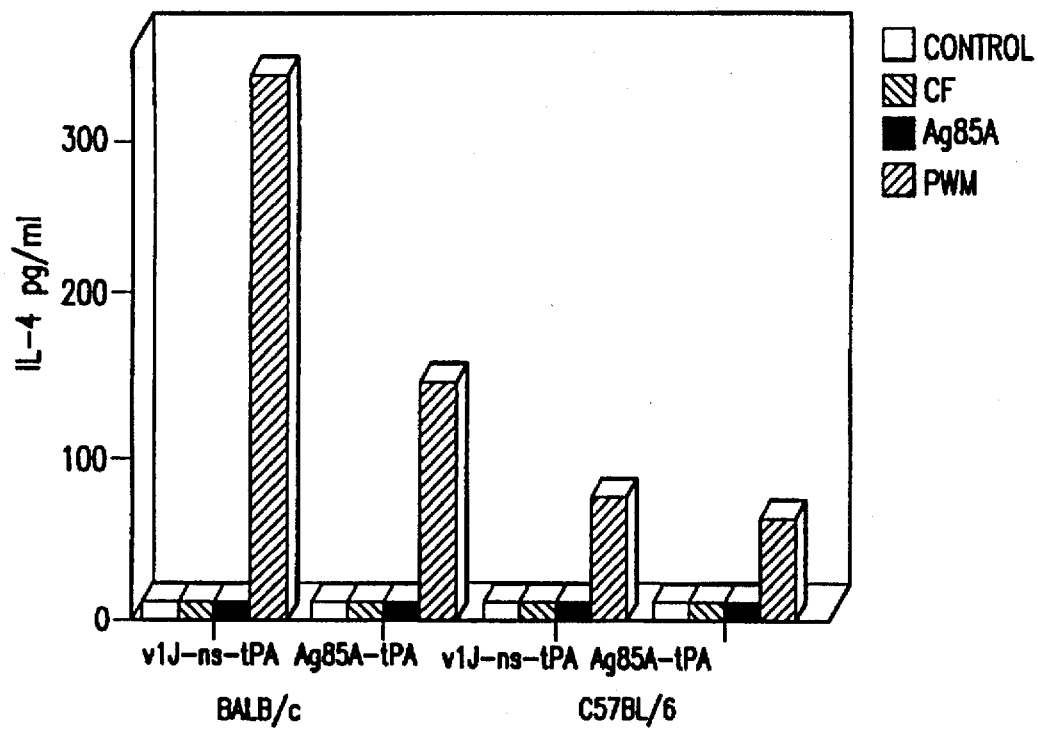
FIG. 14 Lack of IL-4 production in BALB/c mice by a Tb DNA vaccine is shown.
Figure 15:
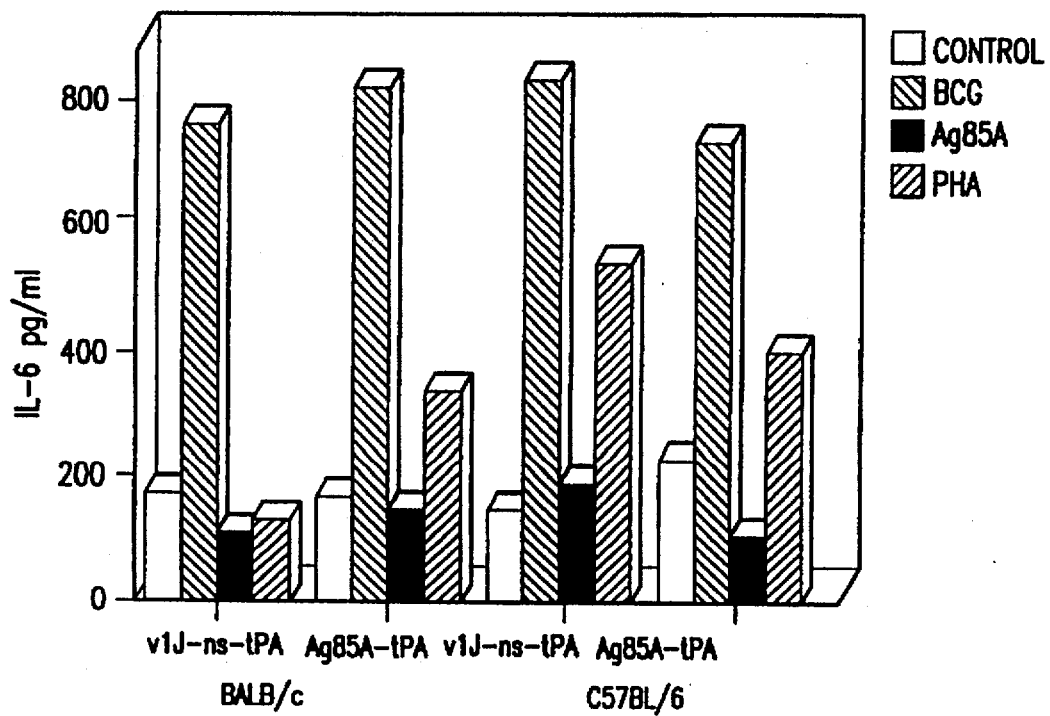
FIG. 15 Lack of IL-6 production in mice by a Tb DNA vaccine is shown.
Figure 16:
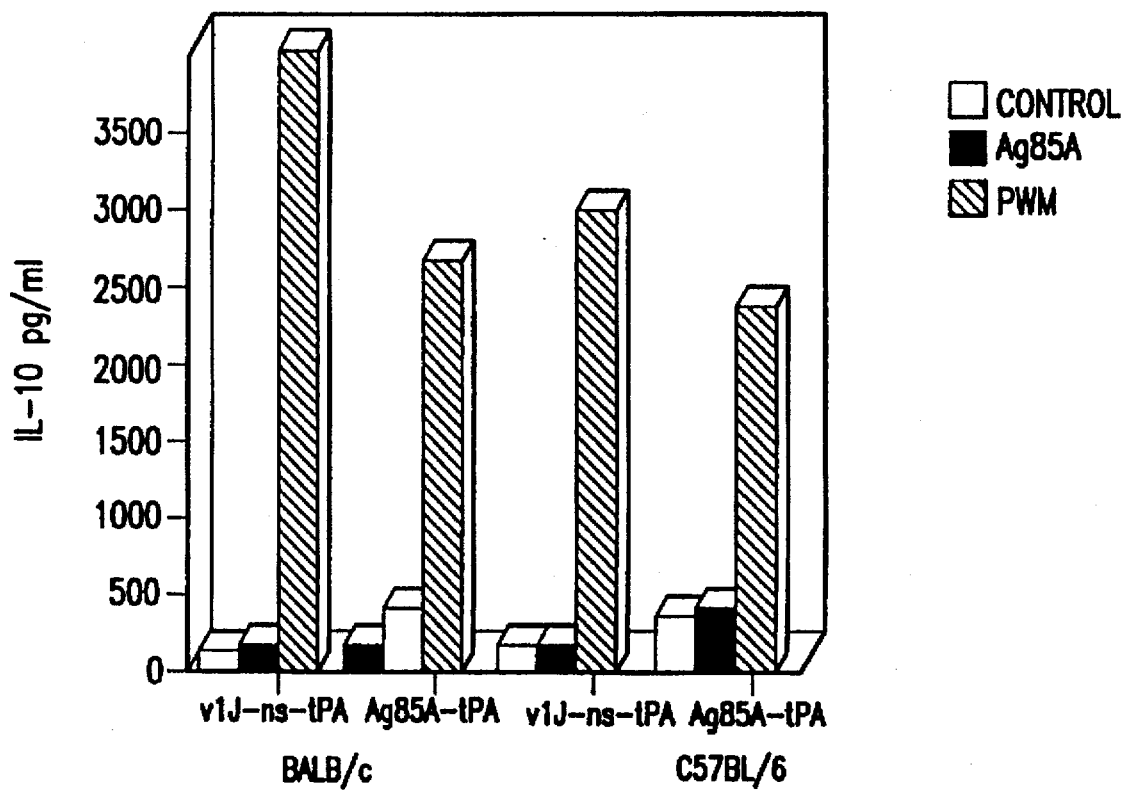
FIG. 16 Lack of IL-10 production in mice by a Tb DNA vaccine is shown.

Spleen cells from vaccinated mice were analyzed for cytokine secretion in response to specific antigen restimulation as described in Huygen et al, 1992 [Infect. Immunity 60, 2880]. Specifically, spleen cells were incubated with culture filtrate (CF) proteins from M. bovis BCG purified antigen 85A or a 20-mer peptide (p25) corresponding to a known T-cell epitope for C57BL/6 mice (amino acids 241–260). Mice were immunized with V1Jns.tPA85A (C1) (100 µg) three times with three week intervals and analyzed 17 days after the final injection. Cytokines were assayed using bio-assays for IL-2, interferon-γ (IFN-γ) and IL-6, and by ELISA for IL-4 and IL-10. Substantial IL-2 and IFN-γ production was observed in both BALB/c and C57BL/6 mice vaccinated with V1Jns.tPA85A (C1) (FIGS. 10–13). Furthermore, C57BL/6 mice also reacted to the H-2b-restricted T-cell epitope (FIG. 13). IL-4, IL-6 and IL-10 levels were not increased in V1Jns.tPA85A-vaccinated mice (FIGS. 14–16). These results indicate that a $T_h1$ type of helper T-cell response was generated by the DNA vaccine.

EXAMPLE 8

Protection from Mycobacterial Challenge

Figure 17:
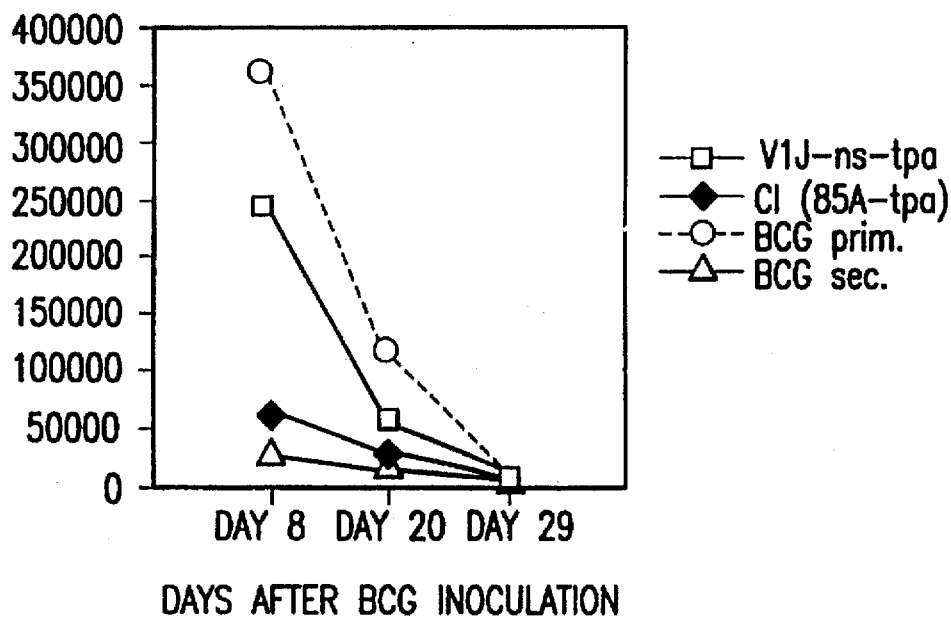
FIG. 17 Reduction of BCG multiplication in lungs of C57BL/6 mice vaccinated with a Tb DNA vaccine is shown.
Figure 18:
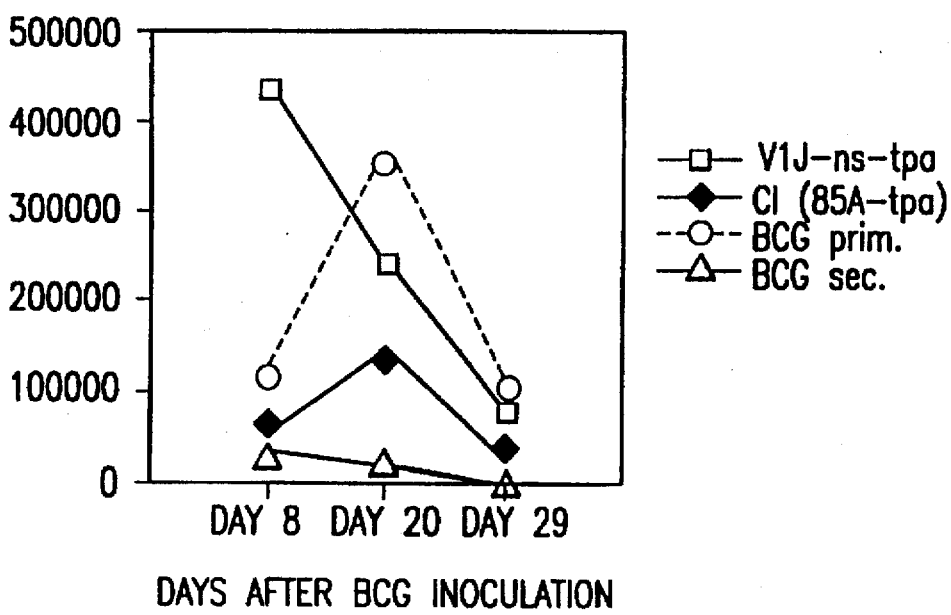
FIG. 18 Reduction of BCG multiplication in lungs of BALB/c mice vaccinated with a Tb DNA vaccine is shown.
Figure 19:
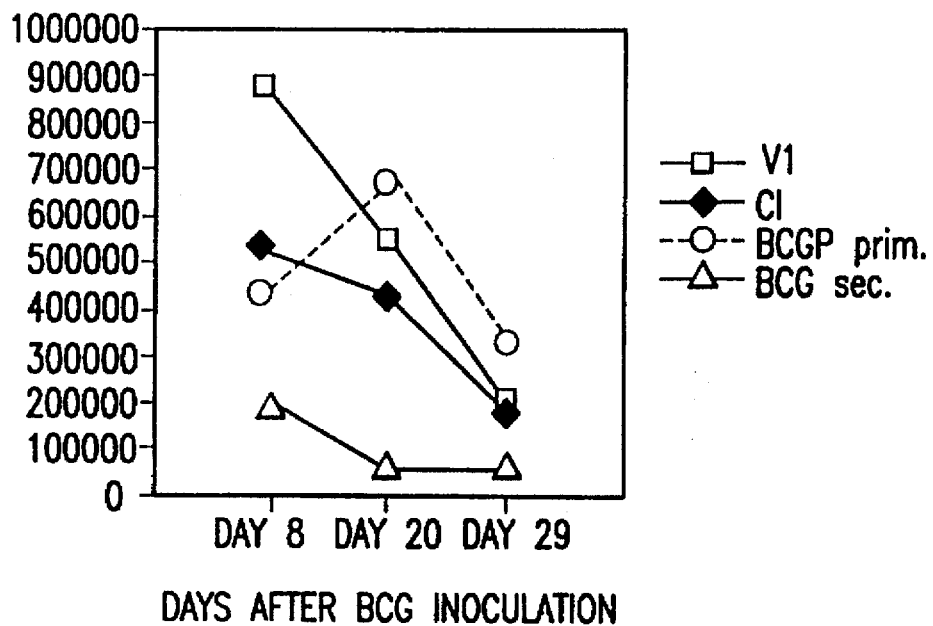
FIG. 19 Reduction of BCG multiplication in spleens of BALB/c mice vaccinated with a Tb DNA vaccine is shown.
Figure 20:
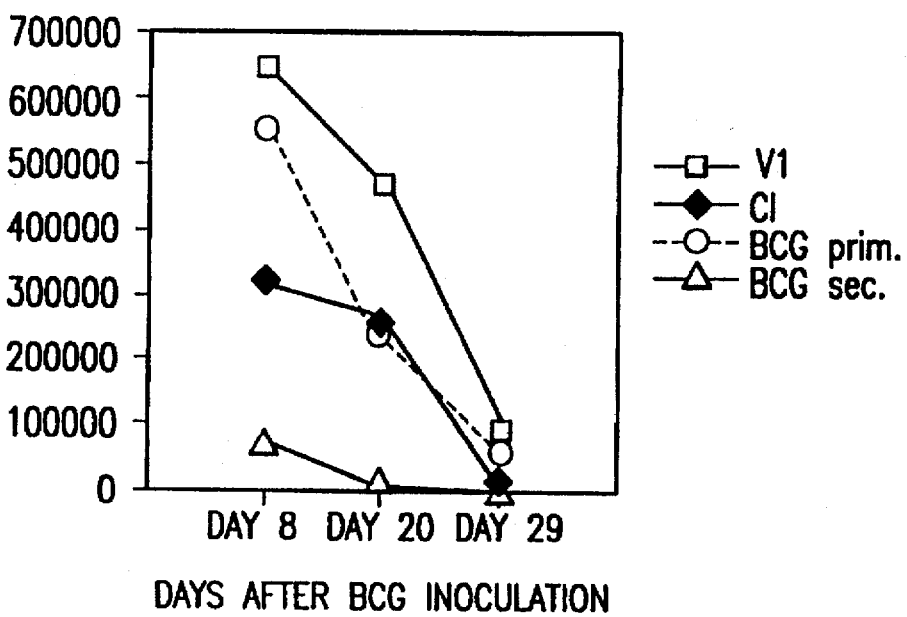
FIG. 20 Reduction of BCG multiplication in spleens of C57BL/6 mice vaccinated with a Tb DNA vaccine is shown.

To test the efficacy of an M.tb DNA vaccine, mice were challenged with an intravenous injection of live M. bovis BCG (0.5 mg) and BCG multiplication was analyzed in the spleens and lungs. As controls, BCG multiplication was measured in challenged naive mice (primary infection) and challenged mice that were vaccinated with BCG at the time of DNA injection (secondary infection). The number of colony-forming units (CFU) in lungs of V1Jns.tPA85A (C1)-vaccinated mice was substantially reduced compared to mice with primary infection or mice vaccinated with control DNA V1J. In C57BL/6 mice, CFU were reduced by 83% on day 8 after challenge (FIG. 17) and in BALB/c mice CFU was reduced by 65% on day 20 (FIG. 18). In spleen, CFU was reduced by approximately 40% at day 20 after challenge in BALB/c mice (FIG. 19) and day 8 in C57BL/6 mice (FIG. 20). Therefore, the immune responses observed after injection of an M.tb DNA vaccine provided protection in a live M. bovis challenge model.

What is claimed is:

1. A DNA vaccine comprising a plasmid vector comprising a nucleotide sequence encoding an antigen 85A mature protein operably linked to transcription regulatory elements, wherein upon administration into a mammal free from infection with *Mycobacterium tuberculosis* or *Mycobacte-*

*rium bovis* said mammal is protected from infection by *Mycobacterium tuberculosis* or *Mycobacterium bovis*.

2. The DNA vaccine of claim 1 wherein the plasmid is V1Jns-85A[C2].

3. The DNA vaccine of claim 1 wherein said vaccine is dicistronic, said vaccine further comprising an additional nucleotide sequence encoding an immunomodulatory or immunostimulatory gene, said additional nucleotide sequence being operably linked to regulatory elements.

4. The DNA vaccine of claim 3 wherein said additional nucleotide sequence is selected from the group consisting of nucleotide sequences encoding GM-CSF, IL-12, interferon, and a member of the B7 family of T-cell costimulatory proteins.

5. The DNA vaccine of claim 1 wherein said regulatory elements comprise the Cytomegalovirus promoter with the intron A sequence, and the Bovine Growth Hormone terminator.

6. The DNA vaccine of claim 1 wherein said mammal is a domestic mammal or livestock.

7. The DNA vaccine of claim 1 wherein said nucleotide sequence further encodes a signal sequence operably linked to said antigen 85A mature protein.

8. The DNA vaccine of 7 wherein the plasmid is V1Jns-85A[C3].

9. The DNA vaccine of claim 7 wherein said signal sequence is a eukaryotic signal sequence from the gene encoding human tissue specific plasminogen activator.

10. The DNA vaccine of claim 9 wherein the plasmid is V1Jns-tPA-85A.

11. A method for immunization of a mammal against infection by *Mycobacterium tuberculosis* or *Mycobacterium bovis* comprising the administration of a DNA vaccine comprising a plasmid vector, said plasmid vector comprising a nucleotide sequence encoding an antigen 85A mature protein operably linked to transcription regulatory elements, wherein upon administration into a mammal free from infection with *Mycobacterium tuberculosis* or *Mycobacterium bovis*, said mammal is protected from infection by *Mycobacterium tuberculosis* or *Mycobacterium bovis*.

12. The method of claim 11 wherein said mammal is a domestic mammal or livestock.

13. The method of claim 11 wherein said DNA vaccine is dicistronic, said vaccine further comprising an additional nucleotide sequence encoding an immunomodulatory or immunostimulatory gene, said additional nucleotide sequence being operably linked to regulatory elements.

14. The method of claim 13 wherein said additional nucleotide sequence is selected from the group consisting of nucleotide sequences encoding GM-CSF, IL-12, interferon, and a member of the B7 family of T-cell costimulatory proteins.

15. The method of claim 11 wherein said regulatory elements comprise the Cytomegalovirus promoter with the intron A sequence, and the Bovine Growth Hormone terminator.

16. The method according to claim 11 wherein said nucleotide sequence further encodes a signal sequence operably linked to said antigen 85A mature protein.

17. The method of claim 16 wherein said signal sequence is a eukaryotic signal sequence from the gene encoding human tissue specific plasminogen activator.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTATATAAGC AGAGCTCGTT TAG      2 3

( 2 ) INFORMATION FOR SEQ ID NO:2:

( i ) SEQUENCE CHARACTERISTICS:
        ( A ) LENGTH: 30 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GTAGCAAAGA TCTAAGGACG GTGACTGCAG    30

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTATGTGTCT GAAAATGAGC GTGGAGATTG GGCTCGCAC    39

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTGCGAGCCC AATCTCCACG CTCATTTTCA GACACATAC    39

( 2 ) INFORMATION FOR SEQ ID NO:5:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GATCACCATG GATGCAATGA AGAGAGGGCT CTGCTGTGTG CTGCTGCTGT GTGGAGCAGT    60

CTTCGTTTCG CCCAGCGA    78

( 2 ) INFORMATION FOR SEQ ID NO:6:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GATCTCGCTG GGCGAAACGA AGACTGCTCC ACACAGCAGC AGCACACAGC AGAGCCCTCT    60

CTTCATTGCA TCCATGGT    78

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:7:

GTACCTCATG AGCCACATAA TACCATG    27

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGTACAAGAT CTACCATGGC TTGCAATTGT CAGTTGATGC    40

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CCACATAGAT CTCCATGGGA ACTAAAGGAA GACGGTCTGT TC    42

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GGTACAAATA TTGGCTATTG GCCATTGCAT ACG    33

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CCACATCTCG AGGAACCGGG TCAATTCTTC AGCACC    36

( 2 ) INFORMATION FOR SEQ ID NO:12:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GGTACAGATA  TCGGAAAGCC  ACGTTGTGTC  TCAAAATC                                    38
```

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CCACATGGAT  CCGTAATGCT  CTGCCAGTGT  TACAACC                                     37
```

( 2 ) INFORMATION FOR SEQ ID NO:14:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GGTACATGAT  CACGTAGAAA  AGATCAAAGG  ATCTTCTTG                                   39
```

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CCACATGTCG  ACCCGTAAAA  AGGCCGCGTT  GCTGG                                       35
```

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GGAAGATCTT  TTCCCGGCCG  GGCTTGCCG                                               29
```

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
GGAAGATCTT  GTCTGTTCGG  AGCTAGGC                                                28
```

( 2 ) INFORMATION FOR SEQ ID NO:18:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

GGAAGATCTA CCATGGGCTT TTCCCGGCCG GGCTTGC 37

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GGAAGATCTA CCATGGCACA GCTTGTTGAC AGGGTT 36

( 2 ) INFORMATION FOR SEQ ID NO:20:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GGAAGATCTC CTTCTCCCGG CCGGGGCTGC CGGTCGAG 38

( 2 ) INFORMATION FOR SEQ ID NO:21:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GGAAGATCTA ACCTTCGGTT GATCCCGTCA GCC 33

( 2 ) INFORMATION FOR SEQ ID NO:22:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GGAAGATCTC CTTCTCTAGG CCCGGTCTTC CA 32

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:23:

GGAAGATCTT GCCGATGCTG GCTTGCTGGC TCAGGC                                        36

(2) INFORMATION FOR SEQ ID NO:24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GGAAGATCTA CCATGGGCTT CTCCCGGCCG GGGCTGC                                       37

(2) INFORMATION FOR SEQ ID NO:25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGAAGATCTA CCATGGGCTT CTCTAGGCCC GGTCTTC                                       37

(2) INFORMATION FOR SEQ ID NO:26:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

GTCACCGTCC TTGAGATCAC CATGGATGCA ATGAAGAGAG GGCTCTGCTG TGTGCTGCTG             60

CTGTGTGGAG CAGTCTTCGT TTCGCCCAGC GAGATCTTTT CCCGGCCGGG CTTGCCGGTG            120

GAGTAC                                                                       126

(2) INFORMATION FOR SEQ ID NO:27:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:27:

Met Asp Ala Met Lys Arg Gly Leu Cys Cys Val Leu Leu Leu Cys Gly
 1               5                  10                  15

Ala Val Phe Val Ser Pro Ser Glu Ile Phe Ser Arg Pro Gly Leu Pro
                20                  25                  30

Val Glu Tyr
        35

( 2 ) INFORMATION FOR SEQ ID NO:28:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

```
GTCACCGTCC TTGAGATCTA CCATGGGCTT TTCCCGGCCG GGCTTGCCGG TGGAGTAC          58
```

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: N-terminal ( x i ) SEQUENCE DESCRIPTION: SEQ ID NO:29:

```
Met Gly Phe Ser Arg Pro Gly Leu Pro Val Glu Tyr
 1               5                  10
```

( 2 ) INFORMATION FOR SEQ ID NO:30:

( i ) SEQUENCE CHARACTERISTICS:
        ( A ) LENGTH: 174 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

```
CTGCAGTCAC CGTCCTTGAG ATCTACCATG GCACAGCTTG TTGACAGGGT TCGTGGCGCC         60
GTCACGGGTA TGTCGCGTCG ACTCGTGGTC GGGGCCGTCG GCGCGGCCCT AGTGTCGGGT        120
CTGGTCGGCG CCGTCGGTGG CACGGCGACC GCGGGGGCAT TTCCCGGCC GGGC              174
```

( 2 ) INFORMATION FOR SEQ ID NO:31:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: N-terminal ( x i ) SEQUENCE DESCRIPTION: SEQ ID NO:31:

```
Met Ala Gln Leu Val Asp Arg Val Arg Gly Ala Val Thr Gly Met Ser
 1               5                  10                  15
Arg Arg Leu Val Val Gly Ala Val Gly Ala Ala Leu Val Ser Gly Leu
                20                  25                  30
Val Gly Ala Val Gly Gly Thr Ala Thr Ala Gly Ala Phe Ser Arg Pro
                35                  40                  45
Gly
```

( 2 ) INFORMATION FOR SEQ ID NO:32:

( i ) SEQUENCE CHARACTERISTICS:
　　　　( A ) LENGTH: 116 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( x i ) SEQUENCE DESCRIPTION: SEQ ID NO:32:

```
CTGCAGTCAC CGTCCTTGAG ATCACCATGG ATGCAATGAA GAGAGGGCTC TGCTGTGTGC      60
TGCTGCTGTG TGGAGCAGTC TTCGTTTCGC CCAGCGAGAT CTCCTTCTCC CGGCCG         116
```

( 2 ) INFORMATION FOR SEQ ID NO:33:

( i ) SEQUENCE CHARACTERISTICS:
　　　　( A ) LENGTH: 30 amino acids
　　　　( B ) TYPE: amino acid
　　　　( C ) STRANDEDNESS: single
　　　　( D ) TOPOLOGY: linear ( i i ) MOLECULE TYPE: protein ( v ) FRAGMENT TYPE: N-terminal ( x i ) SEQUENCE DESCRIPTION: SEQ ID NO:33:

```
Met Asp Ala Met Lys Arg Gly Leu Cys Cys Val Leu Leu Leu Cys Gly
 1               5                  10                  15
Ala Val Phe Val Ser Pro Ser Glu Ile Ser Phe Ser Arg Pro
                20                  25                  30
```

( 2 ) INFORMATION FOR SEQ ID NO:34:

( i ) SEQUENCE CHARACTERISTICS:
　　　　( A ) LENGTH: 116 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( x i ) SEQUENCE DESCRIPTION: SEQ ID NO:34:

```
CTGCAGTCAC CGTCCTTGAG ATCACCATGG ATGCAATGAA GAGAGGGCTC TGCTGTGTGC      60
TGCTGCTGTG TGGAGCAGTC TTCGTTTCGC CCAGCGAGAT CTCCTTCTCT AGGCCC         116
```

( 2 ) INFORMATION FOR SEQ ID NO:35:

( i ) SEQUENCE CHARACTERISTICS:
　　　　( A ) LENGTH: 30 amino acids
　　　　( B ) TYPE: amino acid
　　　　( C ) STRANDEDNESS: single
　　　　( D ) TOPOLOGY: linear ( i i ) MOLECULE TYPE: protein ( v ) FRAGMENT TYPE: N-terminal ( x i ) SEQUENCE DESCRIPTION: SEQ ID NO:35:

```
Met Asp Ala Met Lys Arg Gly Leu Cys Cys Val Leu Leu Leu Cys Gly
 1               5                  10                  15
Ala Val Phe Val Ser Pro Ser Glu Ile Ser Phe Ser Arg Pro
                20                  25                  30
```